United States Patent
Kamal et al.

(10) Patent No.: US 9,951,049 B2
(45) Date of Patent: Apr. 24, 2018

(54) PYRAZOLE LINKED BENZIMIDAZOLE CONJUGATES AND A PROCESS FOR PREPARATION THEREOF

(71) Applicant: Council of Scientific & Industrial Reseach, New Delhi (IN)

(72) Inventors: Ahmed Kamal, Hyderabad (IN); Anver Basha Shaik, Hyderabad (IN); Gajjela Bharath Kumar, Hyderabad (IN); Vangala Santhosh Reddy, Hyderabad (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/709,663

(22) Filed: May 12, 2015

(65) Prior Publication Data

US 2015/0329527 A1 Nov. 19, 2015

(30) Foreign Application Priority Data

May 15, 2014 (IN) .............................. 1295/DEL/2014

(51) Int. Cl.
*C07D 403/04* (2006.01)
*C07D 405/14* (2006.01)

(52) U.S. Cl.
CPC ......... *C07D 403/04* (2013.01); *C07D 405/14* (2013.01)

(58) Field of Classification Search
CPC ............................ C07D 403/04; C07D 405/14
USPC ........................................................ 548/306.1
See application file for complete search history.

(56) References Cited

U.S. PATENT DOCUMENTS

| | | | | |
|---|---|---|---|---|
| 4,440,767 A * | 4/1984 | Fliri | ..................... | C07D 231/12 514/206 |
| 4,495,195 A * | 1/1985 | Beck | ..................... | C07D 231/14 514/406 |

FOREIGN PATENT DOCUMENTS

WO WO-2014-134306 A1 * 9/2014 ........... C07D 403/04

OTHER PUBLICATIONS

Mamedov et al., Russian Chemical Bulletin, 2010, 59(8), pp. 1645-1655.*
Rajora et al., Rasayan Journal of Chemistry, 2009, 2(3), pp. 655-658.*
Mamedov et al., Tetrahedron Letters, 2009, 50(37), pp. 5186-5189.*
Essassi et al., Bulletin des Societes Chimiques Beiges, 1987, 96(1), pp. 63-67.*
An English translation of Essassi et al., Bulletin des Societes Chimiques Belges, 1987, 96(1), pp. 63-67.*
Chemical Abstracts Registry No. 109073-64-5, indexed in the Registry file on STN CAS Online Jul. 11, 1987.*
Chemical Abstracts Registry No. 109073-65-6, indexed in the Registry file on STN CAS Online Jul. 11, 1987.*
Chemical Abstracts Registry No. 109107-19-9, indexed in the Registry file on STN CAS Online Jul. 11, 1987.*
Chen et al., "Discovery of Novel 2-Aryl-4-benzoyl-iidazoles Targeting the Colchicines Binding Site in Tubulin As Potential Anticancer Agents", J. Med. Chem., 2010, 53, pp. 7414-7427.
Congiu et al., "Synthesis and in vitro antitumor activity of new 4,5-dihydropyrazole derivatives", Bioorganic & Medicinal Chemistry, 2010, 18, pp. 6238-6248.
El-Dakdouki et al., "Hypoxia Activated Prodrugs of a 9-Aza-anthrapyrazole Derivative That Has Promising Anticancer Activity", J. Med. Chem., 2011, 54, pp. 8224-8227.
Festa et al., "Solomonamides A and B, New Anti-inflammatory Peptides from *Theonella swinhoei*", Organic Letters, 2011, vol. 13, No. 6, pp. 1532-1535.
Kamal et al., "Synthesis of terphenyl benzimidazoles as tubulin polymerization inhibitors", European Journal of Medicinal Chemistry, 2012, 50, pp. 9-17.
Li et al., "Biological Activity of 4-Substituted Methoxybenzoyl-Aryl-Thiazole: An Active Microtubule Inhibitor", Cancer Res., Jan. 1, 2011, 71(1), pp. 216-224.
Li et al., "Discovery of benzimidazole derivatives as novel multi-target EGFR, VEGFR-2 and PDGFR kinase inhibitors", Bioorganic & Medicinal Chemistry, 2011, 19, pp. 4529-4535.
Salamoun et al., "Synthesis of Heterocyclic Triads by Pd-Catalyzed Cross-Couplings and Evaluation of Their Cell-Specific Toxicity Profile", Org. Lett., 2014, 16, pp. 2034-2037.
Thaher et al., "Tri- and Tetrasubstituted Pyrazole Derivates: Regioisomerism Switches Activity from p38MAP Kinase to Important Cancer Kinases", J. Med. Chem., 2012, 55, pp. 961-965.
International Preliminary Report on Patentability for International Application No. PCT?IN2013/000716, Sep. 25, 2015.

* cited by examiner

*Primary Examiner* — Laura L. Stockton
(74) *Attorney, Agent, or Firm* — Brian L. Stender; Patterson Thuente Pederson, P.A.

(57) ABSTRACT

Pyrazole linked benzimidazole conjugates and a method for synthesis of one or more compounds having a pyrazole linked benzimidazole conjugate, particularly pyrazole linked benzimidazole conjugates that are useful as potential antitumor agents against human cancer cell lines, such as leukemia, non-small cell lung cancer, colon cancer, CNS cancer, melanoma, ovarian cancer, renal cancer, prostate cancer and breast cancer. The process comprises the step of oxidative cyclization of o-phenylenediamines and 3-phenyl-1H-pyrazole-5-carbaldehydes with sodium metabisulphite in ethanol/methanol solvent system at a desired temperature for a period of time to obtain the pyrazole linked benzimidazole conjugate.

6 Claims, No Drawings

PYRAZOLE LINKED BENZIMIDAZOLE CONJUGATES AND A PROCESS FOR PREPARATION THEREOF

RELATED APPLICATION

The present application claims priority to Indian Application No. 1295/DEL/2014 filed May 15, 2014, which is incorporated herein in its entirety by reference.

FIELD OF THE INVENTION

The present invention is generally related to pyrazole linked benzimidazole conjugates. The present invention is also generally related to the process for synthesis of one or more compounds having a pyrazole linked benzimidazole conjugate. More particularly the present invention is generally related to the biological evaluation of these compounds having a pyrazole linked benzimidazole conjugate as potential anticancer agents.

BACKGROUND OF THE INVENTION

Microtubules are dynamic polymers of α and β-tubulin present in the Eukaryotic cells that play an important role in most of the fundamental cellular processes such as cell division, motility, transport, and maintenance of cell shape. Colchicines (S1), combretastatin (S2) nocodazole (S3) and podophyllotoxins (S4) are the distinguished compounds that inhibit microtubule assembly by binding at colchicine binding site of the tubulin.

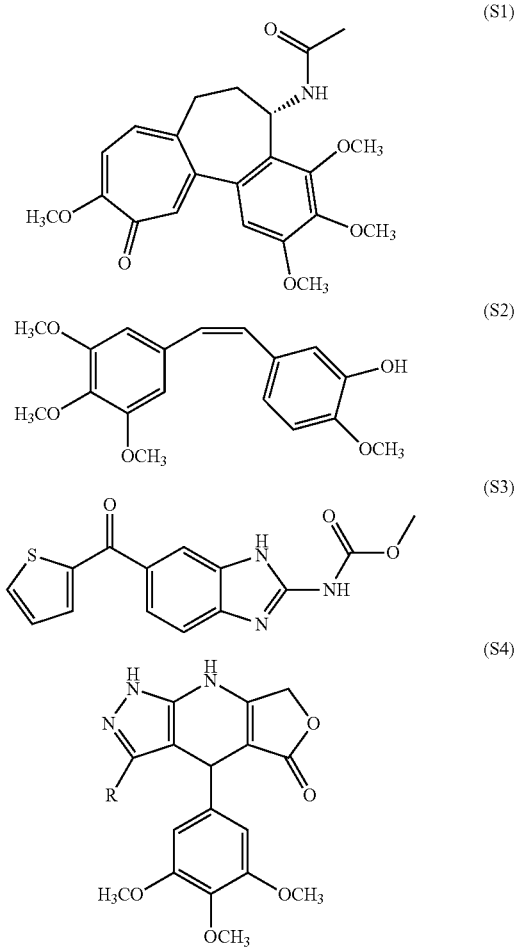

Benzimidazole scaffold is the most privileged structure in the field of medicinal chemistry and this residue is a constituent of vitamin B12 that further supports its potential for their development as therapeutic agents. Recently high-throughput virtual screening was performed wherein 2-aryl benzimidazoles were identified as multi-target EGFR, VEGFR-2 and PDGFR inhibitors with improved therapeutic efficacies. (Li Y, Tan C, Gao C, Zhang C, Luan X, Chen X, Liu H, Chen Y, Jiang Y. Discovery of benzimidazole derivatives as novel multi-target EGFR, VEGFR-2 and PDGFR kinase inhibitors. *Bioorg. Med. Chem.* 2011 19, (15), 4529-4535). A recent report suggests that terphenyl benzimidazoles inhibit the tubulin polymerization with arrest in G2/M phase of cell cycle. (Kamal A, Reddy M K, Shaik T B, Rajender, Srikanth Y V, Reddy V S, Kumar G B, Kalivendi S V. Synthesis of terphenyl benzimidazoles as tubulin polymerization inhibitors. *Eur. J. Med. Chem,* 2012, 50, 9-17). On other hand the pyrazole derivatives received considerable attention owing to their diverse chemotherapeutic potentials including versatile antineoplastic activities and some pyrazoles have been developed as antitumor and antiproliferative agents, they exert anticancer activity by inhibiting different types of enzymes that play major role in cell division. (El-Dakdouki M H, Adamski N, Foster L, Hacker M P, Erhardt P W. Hypoxia activated prodrugs of a 9-aza-anthrapyrazole derivative that has promising anticancer activity. *J. Med. Chem.* 2011, 54, (23), 8224-8227). Moreover tri and tetra substituted pyrazole derivates have been proved to have potent anticancer action due to the inhibition of p38α MAP kinase (Abu Thaher B, Arnsmann M, Totzke F, Ehlert J E, Kubbutat M H, Schächtele C, Zimmermann M O, Koch P, Boeckler F M, Laufer S A. Tri- and tetrasubstituted pyrazole derivates: regioisomerism switches activity from p38MAP kinase to important cancer kinases. *J. Med. Chem.* 2012, 55, (2), 961-965). Many reports suggest that methoxy substituents of combretastatin play a major role in the tubulin depolymerisation process by binding at colchicine binding site, thus incorporating such a component has been utilized extensively to design the pharmacophore that target tubulin (Congiu C, Onnis V, Vesci L, Castorina M, Pisano C. Synthesis and in vitro antitumor activity of new 4,5-dihydropyrazole derivatives. *Bioorg. Med. Chem.* 2010, 18, (17), 6238-6248). The exceptional feature of microtubule-binding agents, in comparison to other categories of anticancer drugs, is their incredible structural complexity and diversity, which provides many possibilities for new scaffold design. Recently, many studies suggested that combination chemotherapy with the drugs that could work by different mechanism. Therefore, conjugates of pyrazole and benzimidazole have been designed to evaluate anticancer activity that could be beneficial for the treatment of cancer.

However, there still remains a need in the industry for effective and novel anticancer drugs.

SUMMARY OF THE INVENTION

According to certain aspects, the present invention provides some new pyrazole-benzimidazole conjugates of Formula A.

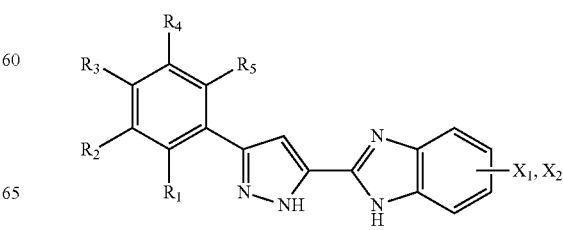

Formula A

In certain aspects of the present invention, substituent $R_1$ in Formula A is chosen from H, Cl, F, $CH_3$, $OCH_3$ and $3,4(OCH_2O)$.

In certain aspects of the present invention, substituent $R_2$ in Formula A is chosen from H, Cl, F, $CH_3$, $OCH_3$ and $3,4(OCH_2O)$.

In certain aspects of the present invention, substituent $R_3$ in Formula A is chosen from H, Cl, F, $CH_3$, $OCH_3$ and $3,4(OCH_2O)$.

In certain aspects of the present invention, substituent $R_4$ in Formula A is chosen from H, Cl, F, $CH_3$, $OCH_3$ and $3,4(OCH_2O)$.

In certain aspects of the present invention, substituent $R_5$ in Formula A is chosen from H, Cl, F, $CH_3$, $OCH_3$ and $3,4(OCH_2O)$.

In certain aspects of the present invention, substituent $X_1$ in Formula A is chosen from H, Br, Cl, F, $CH_3$, $OCH_3$, $NO_2$ and $CF_3$.

In certain aspects of the present invention, substituent $X_2$ in Formula A is chosen from H, Br, Cl, F, $CH_3$, and $CF_3$.

According to certain aspects, the present invention provides pyrazole-benzimidazole conjugate salts of Formula A.

Formula A

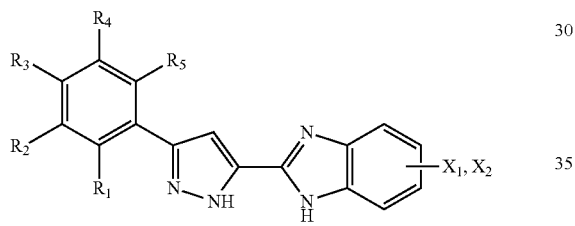

In certain aspects of the present invention, substituents $R_1$, $R_2$, $R_3$, $R_4$ and/or $R_5$ of the pyrazole-benzimidazole conjugate salts of Formula A are chosen from H, Cl, F, $CH_3$, $OCH_3$ and $3,4(OCH_2O)$.

In certain aspects of the present invention, substituent $X_1$ of the pyrazole-benzimidazole conjugate salts of Formula A is chosen from H, Br, Cl, F, $CH_3$, $OCH_3$, $NO_2$ and $CF_3$.

In certain aspects of the present invention, substituent $X_2$ of the pyrazole-benzimidazole conjugate salts of Formula A is chosen from H, Br, Cl, F, $CH_3$, and $CF_3$.

According to certain aspects of the present invention, the pyrazole linked benzimidazole conjugates of Formula 1 provide a process for the preparation of pyrazole-benzimidazole conjugates of Formula A.

Still in other aspects of the present invention, the biological potential of these compounds as potential anticancer agents is evaluated.

In certain other aspects of the present invention, the new pyrazole linked benzimidazole conjugates of Formula A are represented by the compounds of formulae 6a-14a, formulae 6b-14b, formulae 6c-14c, formulae 6d-14d, formulae 6e-14e, formulae 6f-14f, formulae 6g-14g, formulae 6h-14h, formulae 6i-14i, formulae 6j-14j, formulae 6k-14k, formulae 6l-14l, formulae 6m-14m, and formulae 6n-14n, as shown below:

(6a-14a)

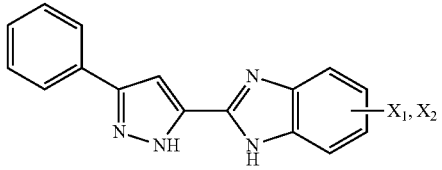

(6b-14b)

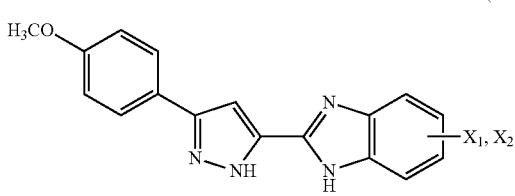

(6c-14c)

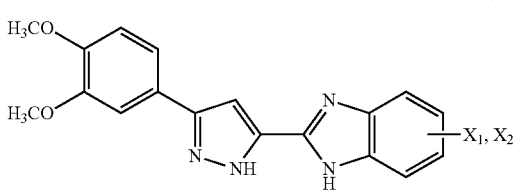

(6d-14d)

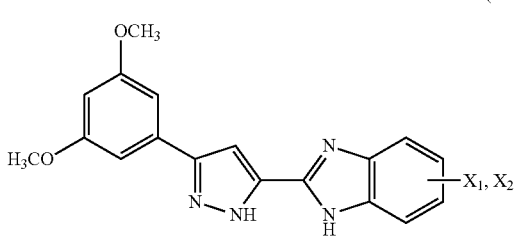

(6e-14e)

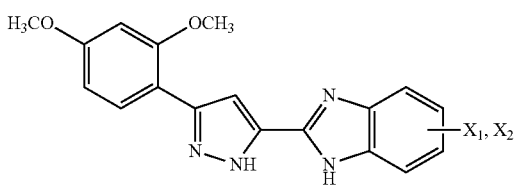

(6f-14f)

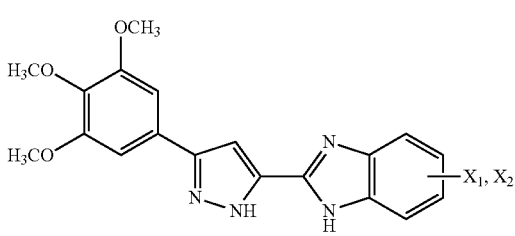

(6g-14g)

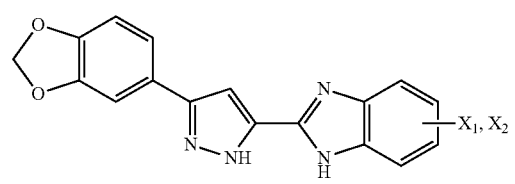

-continued (6h-14h)
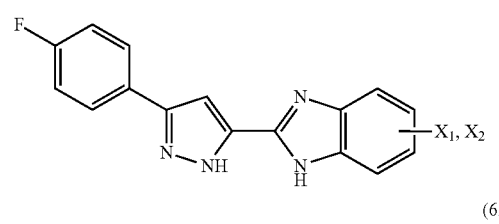

(6i-14i)
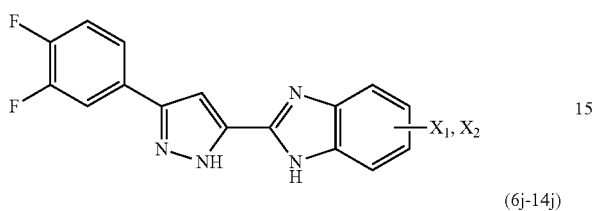

(6j-14j)
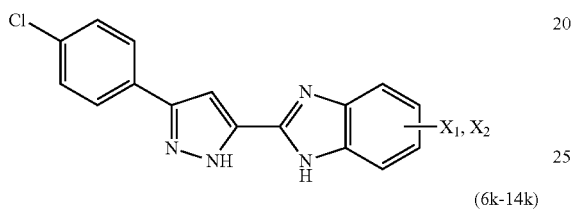

(6k-14k)
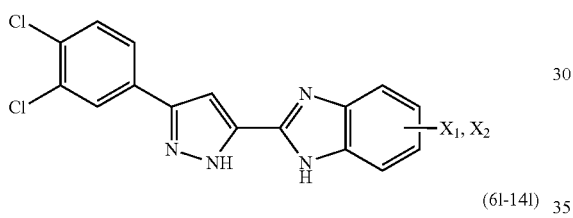

(6l-14l)
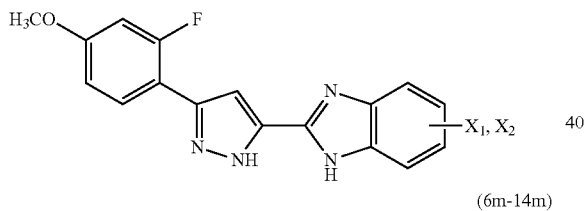

(6m-14m)
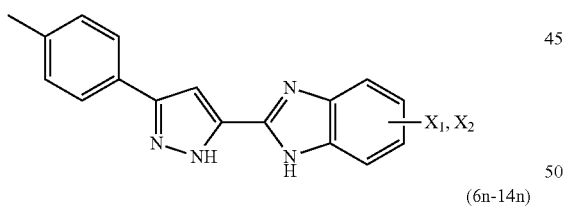

(6n-14n)
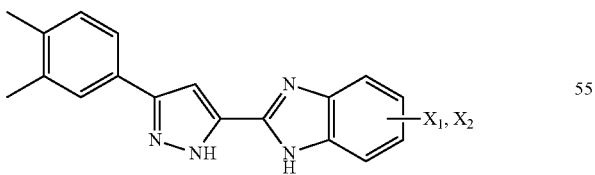

In certain aspects of the present invention, the $X_1$ substituent is chosen from H, Br, Cl, F, CH$_3$, OCH$_3$, NO$_2$ and CF$_3$, and the $X_2$ substituent is chosen from H, Br, Cl, F, CH$_3$, and CF$_3$.

In certain aspects of the present invention, the pyrazole linked benzimidazole conjugates of Formula A are represented by the compounds of formulae 6a-14a, 6b-14b, 6c-14c, 6d-14d, 6e-14e, 6f-14f, 6g-14g, 6h-14h, 6i-14i, 6j-14j, 6k-14k, 6l-14l, 6m-14m, and/or 6n-14n, wherein the representative structures of the foregoing formulae are:

(6a)
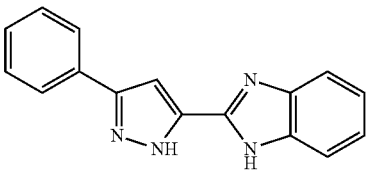

(6b)
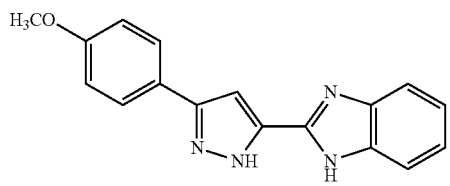

(6c)
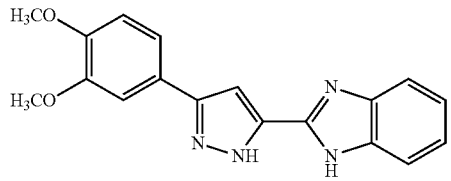

(6d)
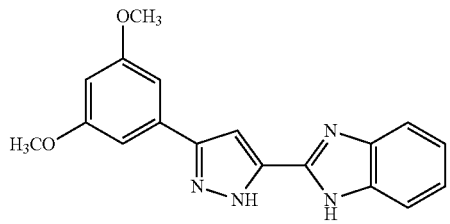

(6e)
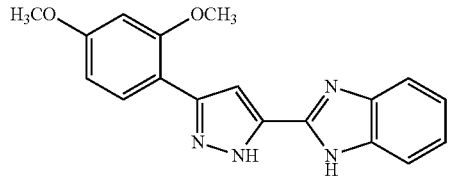

(6f)
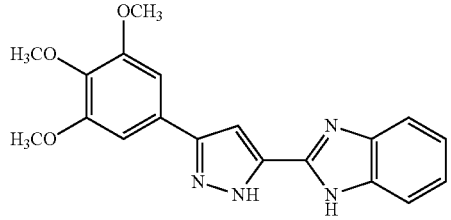

(6g)
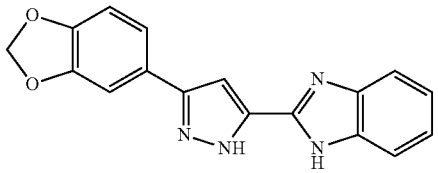

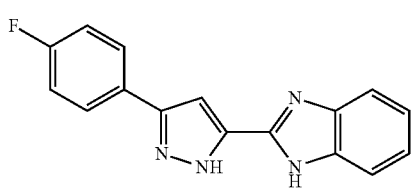 (6h)
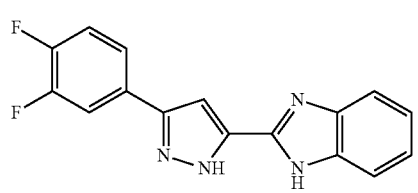 (6i)
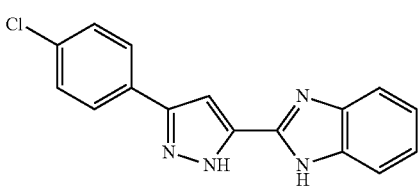 (6j)
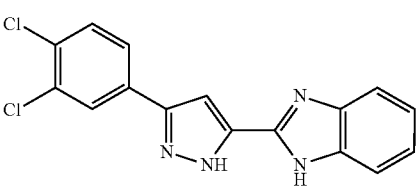 (6k)
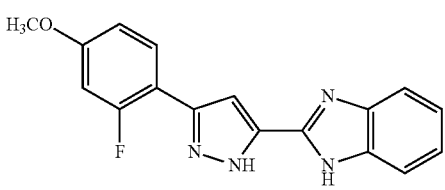 (6l)
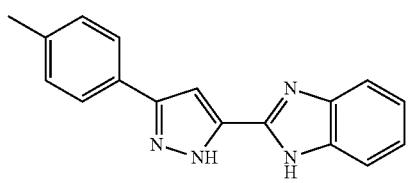 (6m)
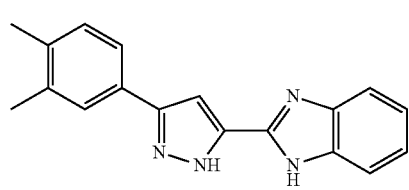 (6n)
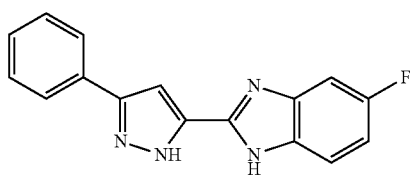 (7a)
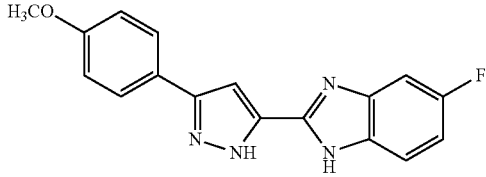 (7b)
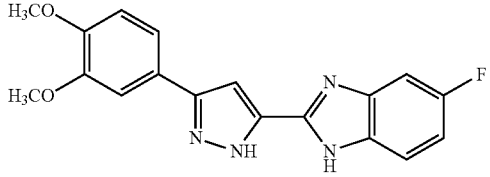 (7c)
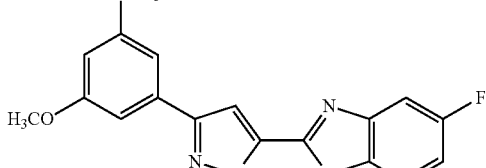 (7d)
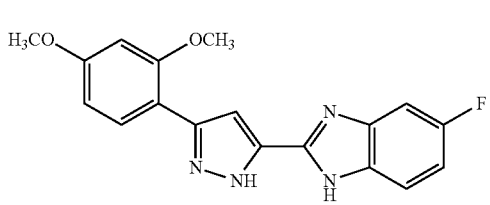 (7e)
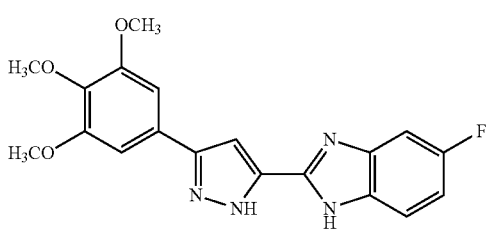 (7f)
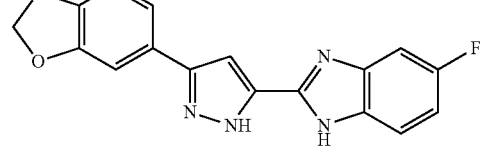 (7g)
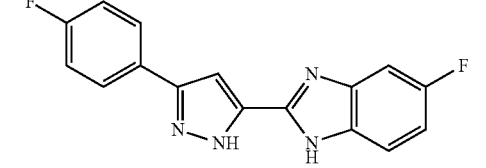 (7h)
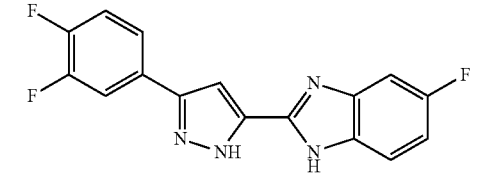 (7i)

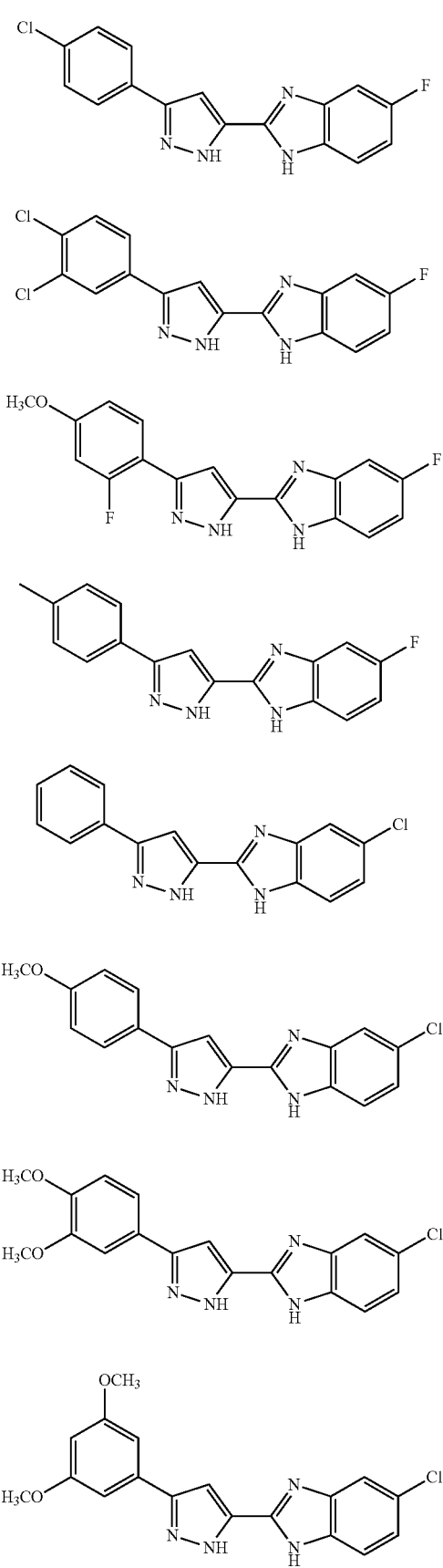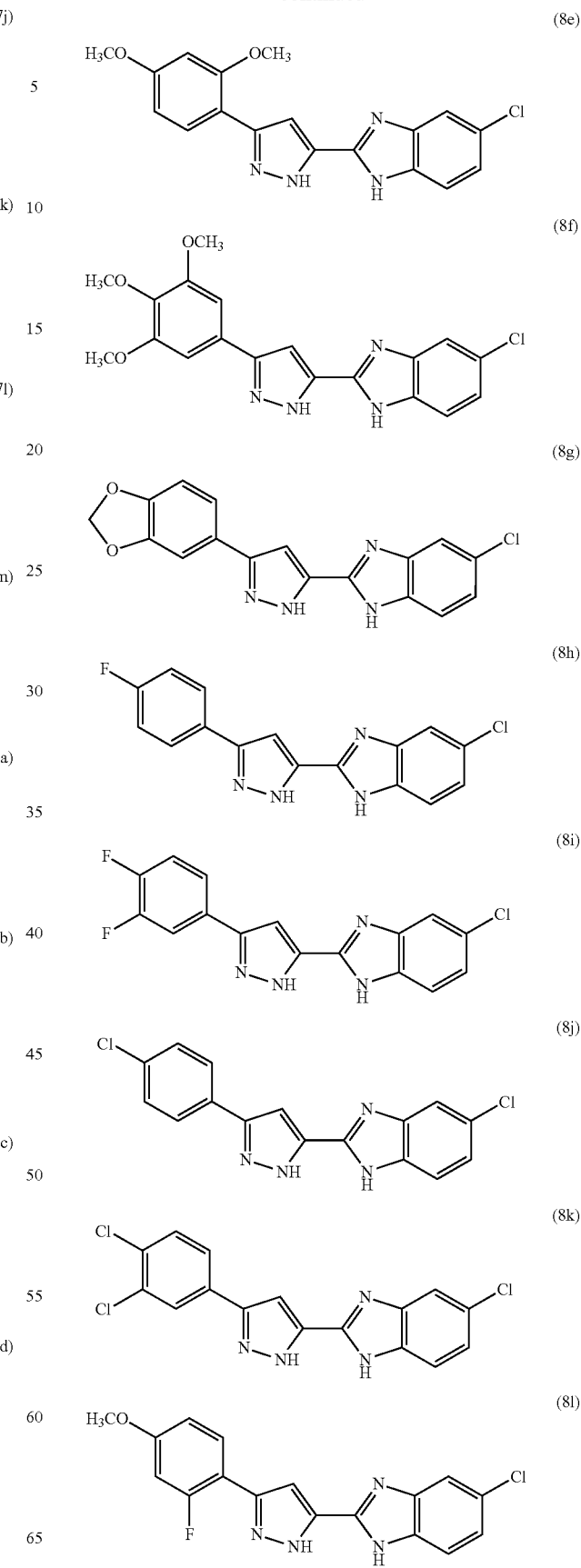

-continued
(8m)
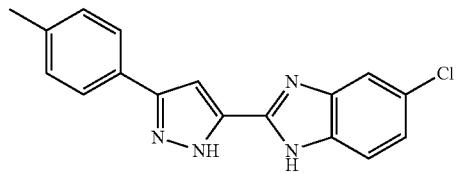
(8n)
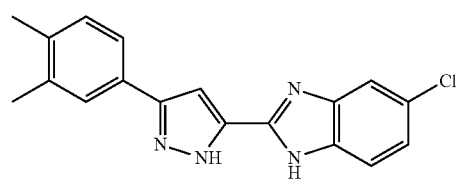
(9a)
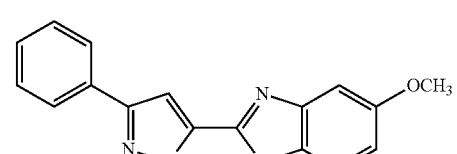
(9b)
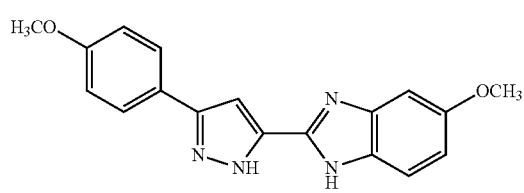
(9c)
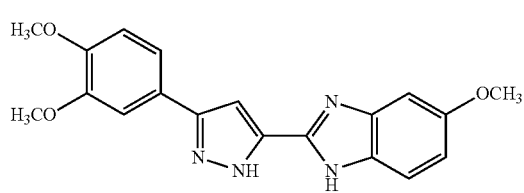
(9d)
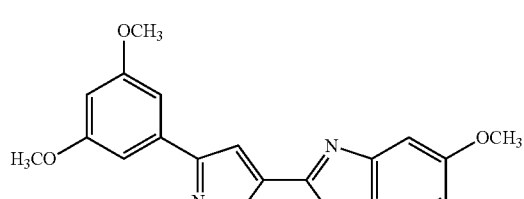
(9e)
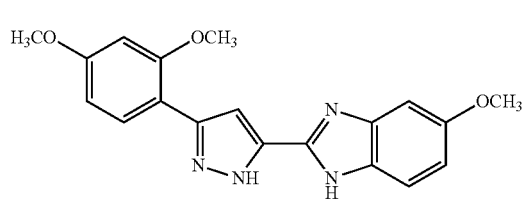
-continued
(9f)
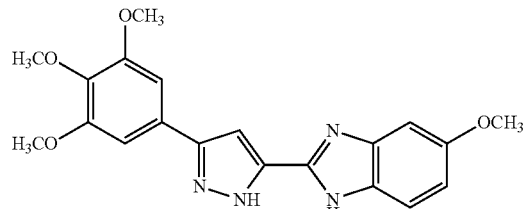
(9g)
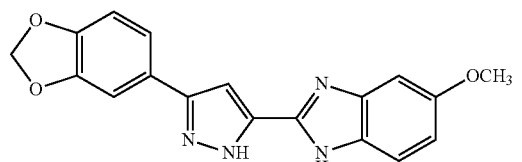
(9h)
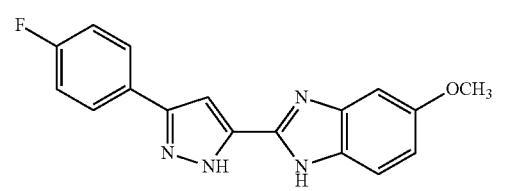
(9i)
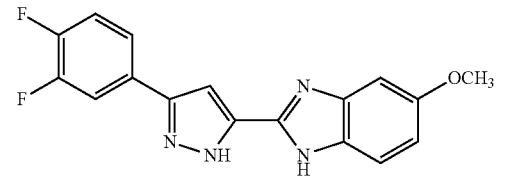
(9j)
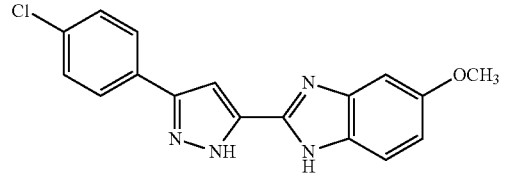
(9k)
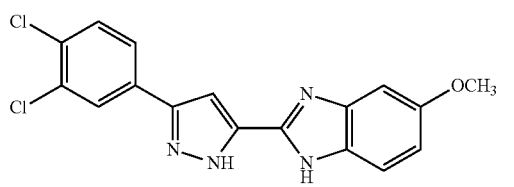
(9l)
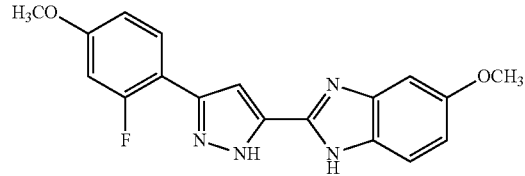
(9m)
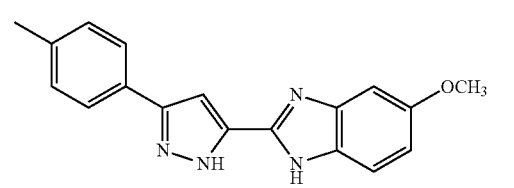

(9n)
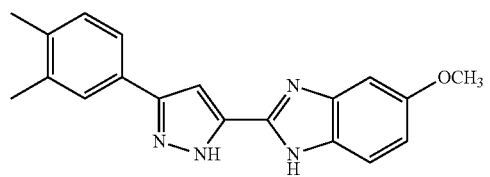
(10a)
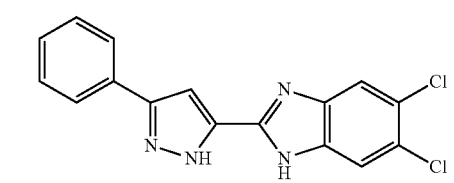
(10b)
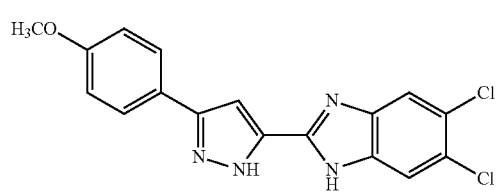
(10c)
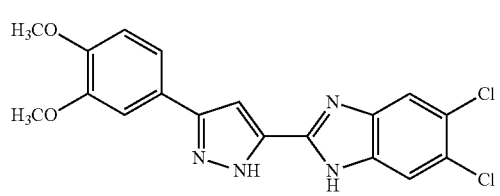
(10d)
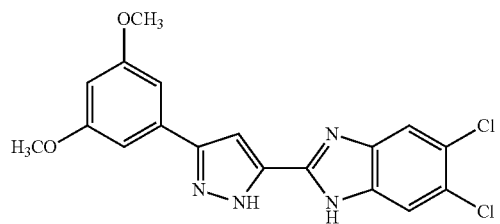
(10e)
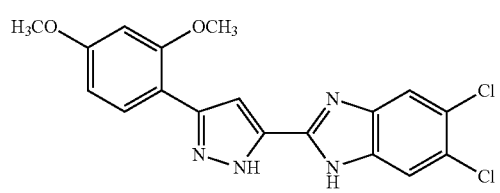
(10f)
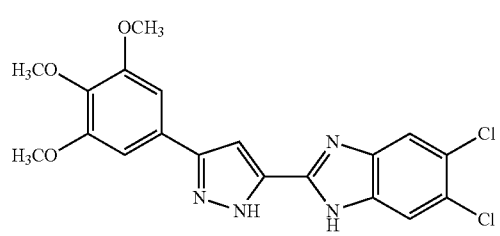
(10g)
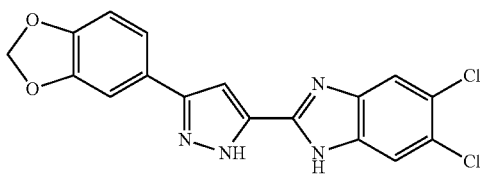
(10h)
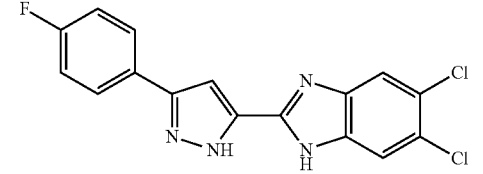
(10i)
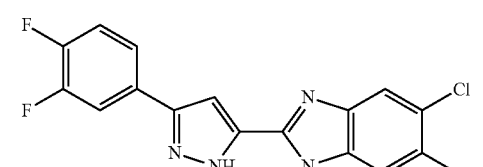
(10j)
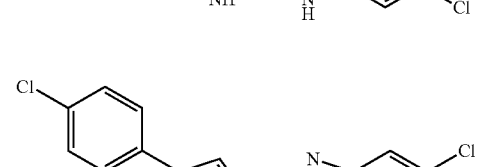
(10k)
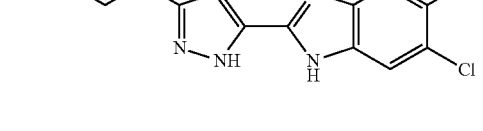
(10l)
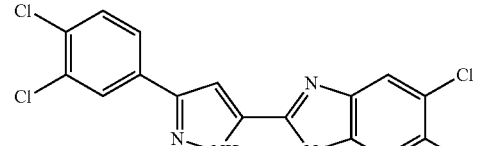
(10m)
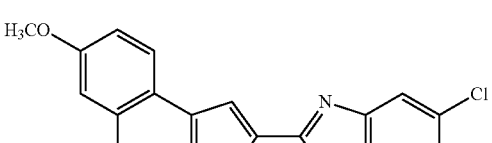
(10n)
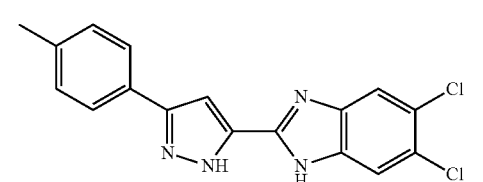
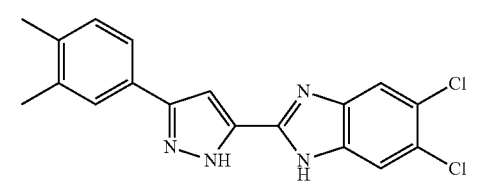

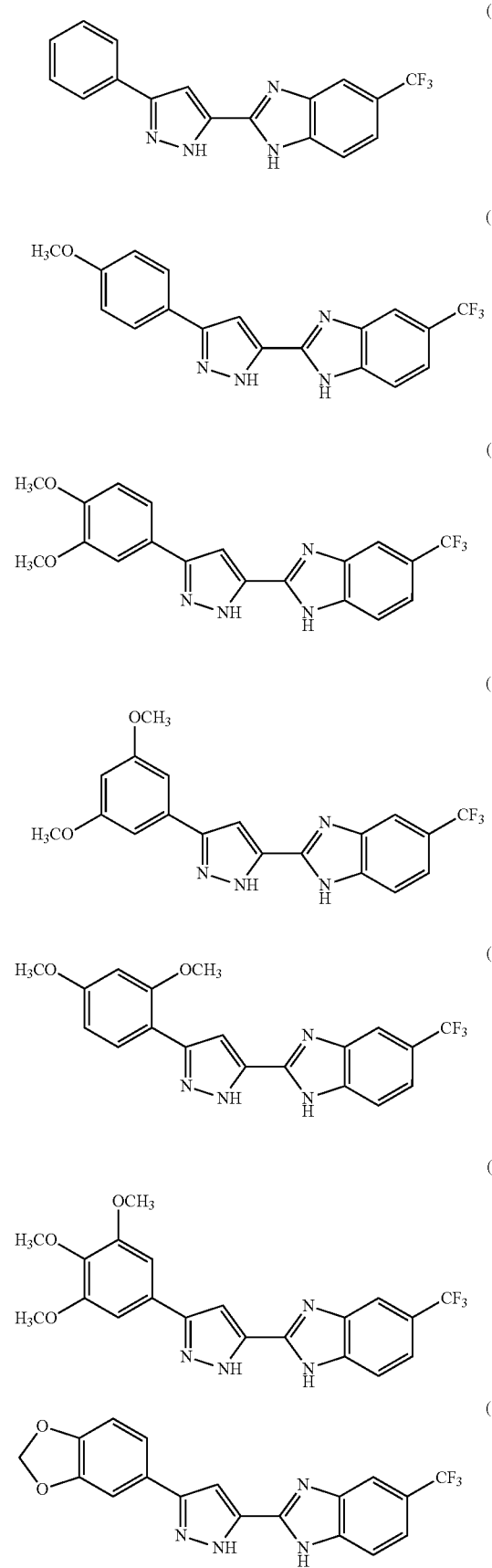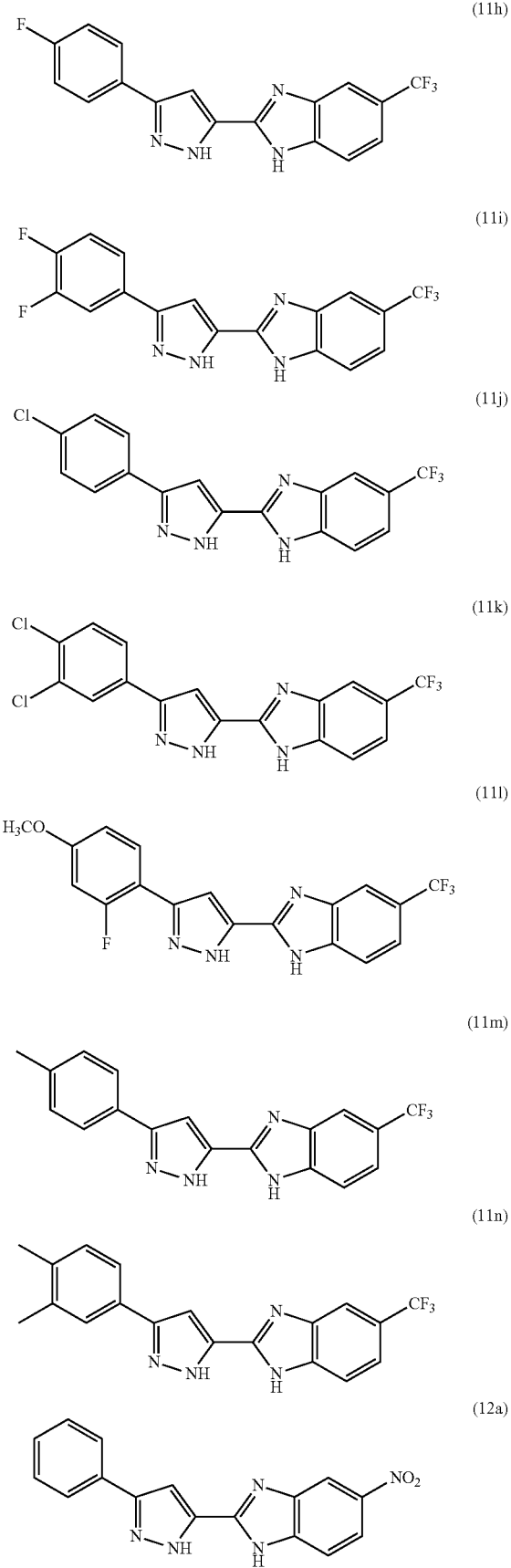

-continued
(12b)
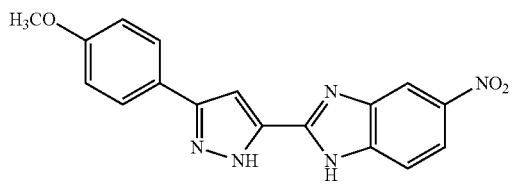
(12c)
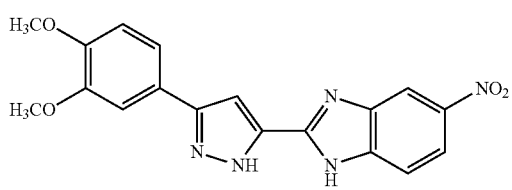
(12d)
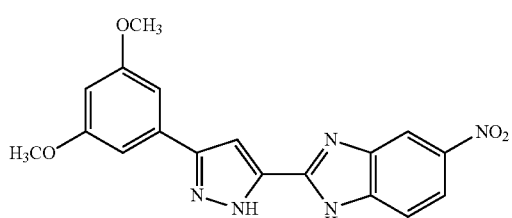
(12e)
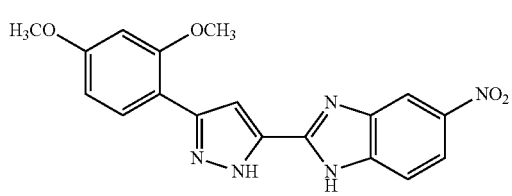
(12f)
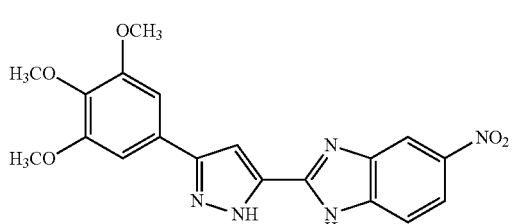
(12g)
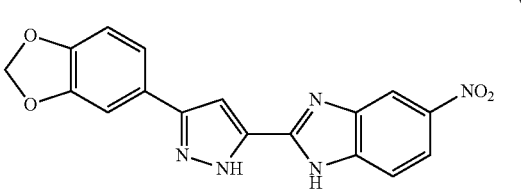
(12h)
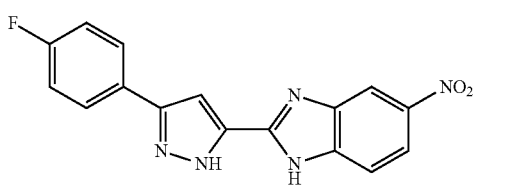
-continued
(12i)
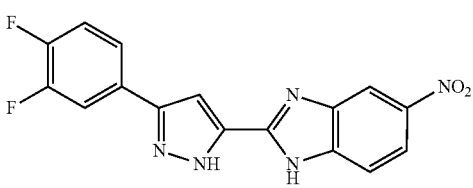
(12j)
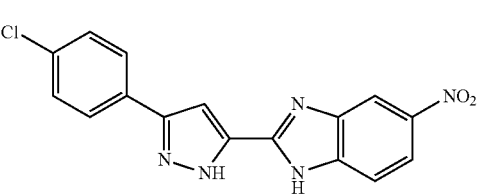
(12k)
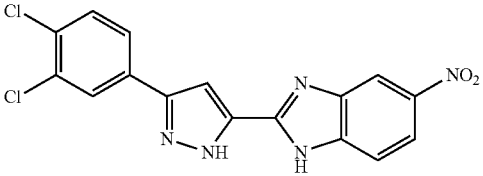
(12l)
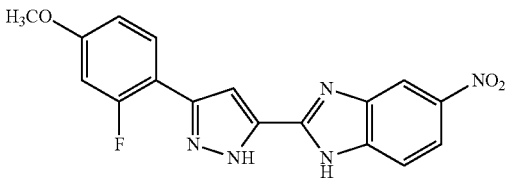
(12m)
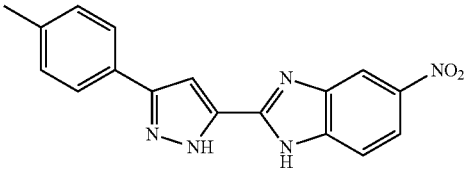
(12n)
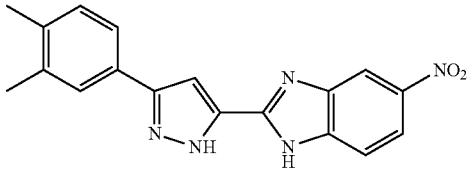
(13a)
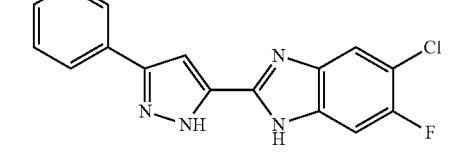
(13b)
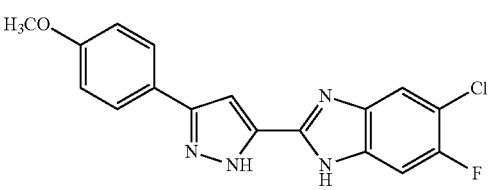

-continued
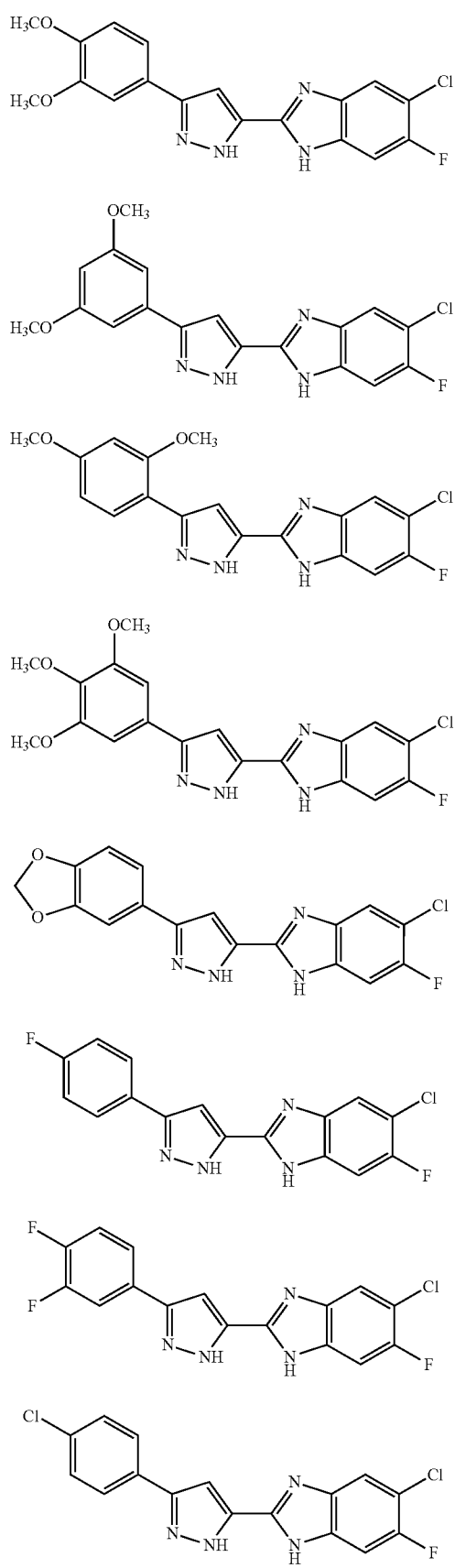
(13c)
(13d)
(13e)
(13f)
(13g)
(13h)
(13i)
(13j)
-continued
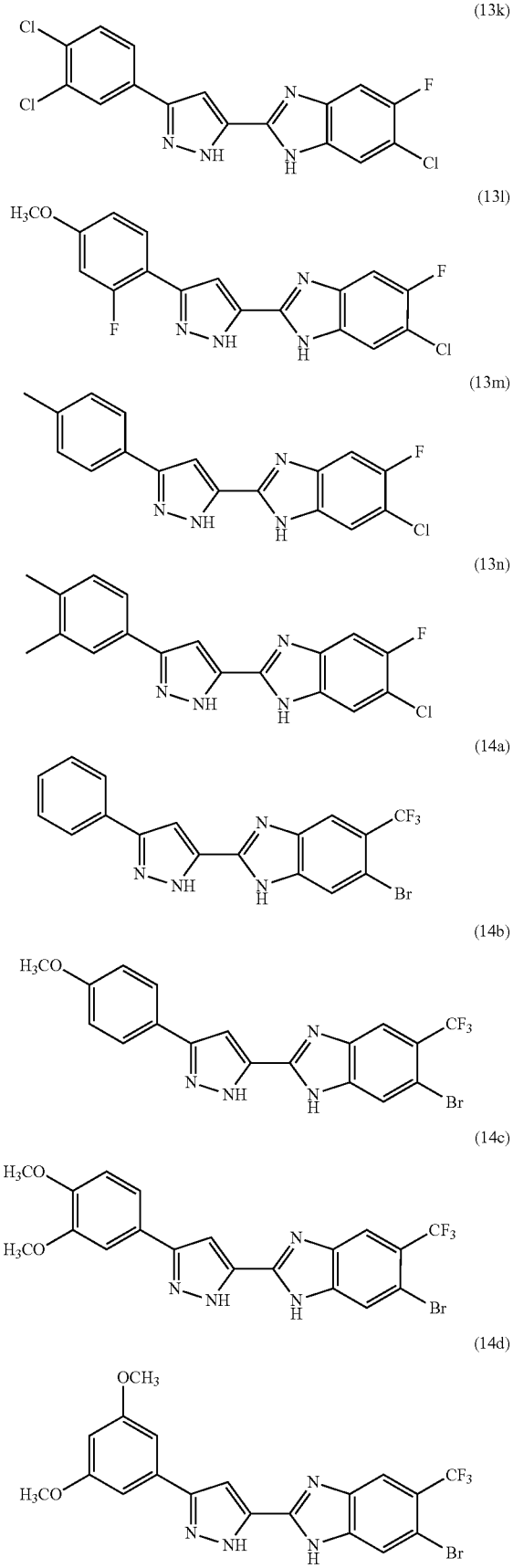
(13k)
(13l)
(13m)
(13n)
(14a)
(14b)
(14c)
(14d)

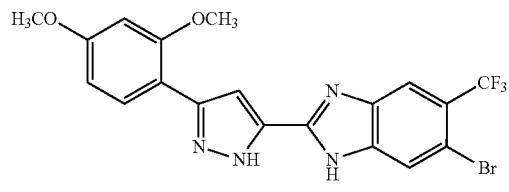
(14e)

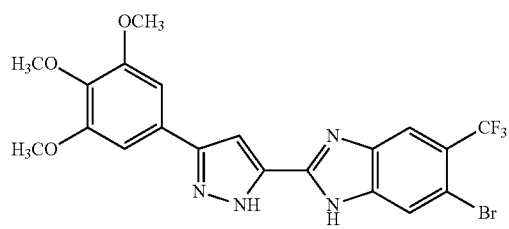
(14f)

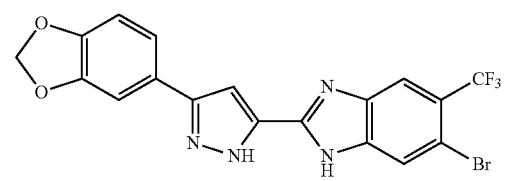
(14g)

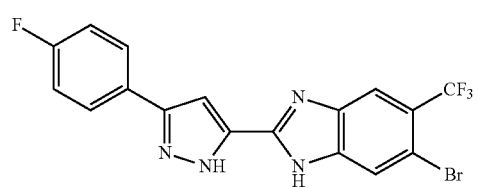
(14h)

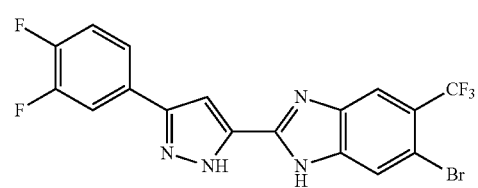
(14i)

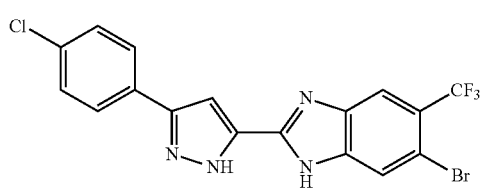
(14j)

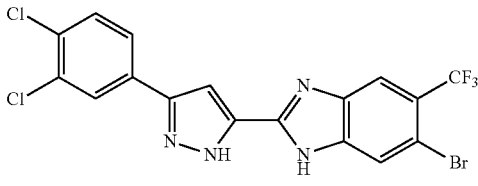
(14k)

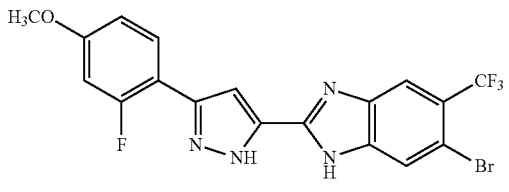
(14l)

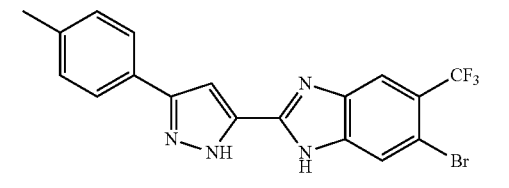
(14m)

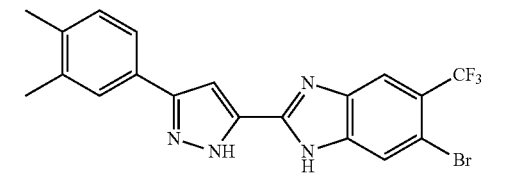
(14n)

In yet certain other aspects, the pyrazole linked benzimidazole conjugates of the present invention are represented by the group of the following compounds:

2-(3-phenyl-1H-pyrazol-5-yl)-1H-benzo[d]imidazole (6a);
2-(3-(4-methoxyphenyl)-1H-pyrazol-5-yl)-1H-benzo[d]imidazole (6b);
2-(3-(3,4-dimethoxyphenyl)-1H-pyrazol-5-yl)-1H-benzo[d]imidazole (6c);
2-(3-(3,5-dimethoxyphenyl)-1H-pyrazol-5-yl)-1H-benzo[d]imidazole (6d);
2-(3-(2,4-dimethoxyphenyl)-1H-pyrazol-5-yl)-1H-benzo[d]imidazole (6e);
2-(3-(3,4,5-trimethoxyphenyl)-1H-pyrazol-5-yl)-1H-benzo[d]imidazole (6f);
2-(3-(benzo[d][1,3]dioxol-5-yl)-1H-pyrazol-5-yl)-1H-benzo[d]imidazole (6g);
2-(3-(4-fluorophenyl)-1H-pyrazol-5-yl)-1H-benzo[d]imidazole (6h);
2-(3-(3,4-difluorophenyl)-1H-pyrazol-5-yl)-1H-benzo[d]imidazole (6i);
2-(3-(4-chlorophenyl)-1H-pyrazol-5-yl)-1H-benzo[d]imidazole (6j);
2-(3-(3,4-dichlorophenyl)-1H-pyrazol-5-yl)-1H-benzo[d]imidazole (6k);
2-(3-(2-fluoro-4-methoxyphenyl)-1H-pyrazol-5-yl)-1H-benzo[d]imidazole (6l);
2-(3-p-tolyl-1H-pyrazol-5-yl)-1H-benzo[d]imidazole (6m);
2-(3-(3,4-dimethylphenyl)-1H-pyrazol-5-yl)-1H-benzo[d]imidazole (6n);
5-fluoro-2-(3-phenyl-1H-pyrazol-5-yl)-1H-benzo[d]imidazole (7a);
5-fluoro-2-(3-(4-methoxyphenyl)-1H-pyrazol-5-yl)-1H-benzo[d]imidazole (7b);
2-(3-(3,4-dimethoxyphenyl)-1H-pyrazol-5-yl)-5-fluoro-1H-benzo[d]imidazole (7c);
2-(3-(3,5-dimethoxyphenyl)-1H-pyrazol-5-yl)-5-fluoro-1H-benzo[d]imidazole (7d);
2-(3-(2,4-dimethoxyphenyl)-1H-pyrazol-5-yl)-5-fluoro-1H-benzo[d]imidazole (7e);

5-fluoro-2-(3-(3,4,5-trimethoxyphenyl)-1H-pyrazol-5-yl)-1H-benzo[d]imidazole (7f);
2-(3-(benzo[d][1,3]dioxol-5-yl)-1H-pyrazol-5-yl)-5-fluoro-1H-benzo[d]imidazole (7g);
5-fluoro-2-(3-(4-fluorophenyl)-1H-pyrazol-5-yl)-1H-benzo[d]imidazole (7h);
2-(3-(3,4-difluorophenyl)-1H-pyrazol-5-yl)-5-fluoro-1H-benzo[d]imidazole (7i);
2-(3-(4-chlorophenyl)-1H-pyrazol-5-yl)-5-fluoro-1H-benzo[d]imidazole (7j);
2-(3-(3,4-dichlorophenyl)-1H-pyrazol-5-yl)-5-fluoro-1H-benzo[d]imidazole (7k);
5-fluoro-2-(3-(2-fluoro-4-methoxyphenyl)-1H-pyrazol-5-yl)-1H-benzo[d]imidazole (7l);
5-fluoro-2-(3-p-tolyl-1H-pyrazol-5-yl)-1H-benzo[d]imidazole (7m);
2-(3-(3,4-dimethylphenyl)-1H-pyrazol-5-yl)-5-fluoro-1H-benzo[d]imidazole (7n);
5-chloro-2-(3-phenyl-1H-pyrazol-5-yl)-1H-benzo[d]imidazole (8a);
5-chloro-2-(3-(4-methoxyphenyl)-1H-pyrazol-5-yl)-1H-benzo[d]imidazole (8b);
5-chloro-2-(3-(3,4-dimethoxyphenyl)-1H-pyrazol-5-yl)-1H-benzo[d]imidazole (8c);
5-chloro-2-(3-(3,5-dimethoxyphenyl)-1H-pyrazol-5-yl)-1H-benzo[d]imidazole (8d);
5-chloro-2-(3-(2,4-dimethoxyphenyl)-1H-pyrazol-5-yl)-1H-benzo[d]imidazole (8e);
5-chloro-2-(3-(3,4,5-trimethoxyphenyl)-1H-pyrazol-5-yl)-1H-benzo[d]imidazole (8f);
2-(3-(benzo[d][1,3]dioxol-5-yl)-1H-pyrazol-5-yl)-5-chloro-1H-benzo[d]imidazole (8g);
5-chloro-2-(3-(4-fluorophenyl)-1H-pyrazol-5-yl)-1H-benzo[d]imidazole (8h);
5-chloro-2-(3-(3,4-difluorophenyl)-1H-pyrazol-5-yl)-1H-benzo[d]imidazole (8i);
5-chloro-2-(3-(4-chlorophenyl)-1H-pyrazol-5-yl)-1H-benzo[d]imidazole (8j);
5-chloro-2-(3-(3,4-dichlorophenyl)-1H-pyrazol-5-yl)-1H-benzo[d]imidazole (8k);
5-chloro-2-(3-(2-fluoro-4-methoxyphenyl)-1H-pyrazol-5-yl)-1H-benzo[d]imidazole (8l);
5-chloro-2-(3-p-tolyl-1H-pyrazol-5-yl)-1H-benzo[d]imidazole (8m);
5-chloro-2-(3-(3,4-dimethylphenyl)-1H-pyrazol-5-yl)-1H-benzo[d]imidazole (8n);
5-methoxy-2-(3-phenyl-1H-pyrazol-5-yl)-1H-benzo[d]imidazole (9a);
5-methoxy-2-(3-(4-methoxyphenyl)-1H-pyrazol-5-yl)-1H-benzo[d]imidazole (9b);
2-(3-(3,4-dimethoxyphenyl)-1H-pyrazol-5-yl)-5-methoxy-1H-benzo[d]imidazole (9c);
2-(3-(3,5-dimethoxyphenyl)-1H-pyrazol-5-yl)-5-methoxy-1H-benzo[d]imidazole (9d);
2-(3-(2,4-dimethoxyphenyl)-1H-pyrazol-5-yl)-5-methoxy-1H-benzo[d]imidazole (9e);
5-methoxy-2-(3-(3,4,5-trimethoxyphenyl)-1H-pyrazol-5-yl)-1H-benzo[d]imidazole (9f);
2-(3-(benzo[d][1,3]dioxol-5-yl)-1H-pyrazol-5-yl)-5-methoxy-1H-benzo[d]imidazole (9g);
2-(3-(4-fluorophenyl)-1H-pyrazol-5-yl)-5-methoxy-1H-benzo[d]imidazole (9h);
2-(3-(3,4-difluorophenyl)-1H-pyrazol-5-yl)-5-methoxy-1H-benzo[d]imidazole (9i);
2-(3-(4-chlorophenyl)-1H-pyrazol-5-yl)-5-methoxy-1H-benzo[d]imidazole (9j);
2-(3-(3,4-dichlorophenyl)-1H-pyrazol-5-yl)-5-methoxy-1H-benzo[d]imidazole (9k);
2-(3-(2-fluoro-4-methoxyphenyl)-1H-pyrazol-5-yl)-5-methoxy-1H-benzo[d]imidazole (9l);
5-methoxy-2-(3-p-tolyl-1H-pyrazol-5-yl)-1H-benzo[d]imidazole (9m);
2-(3-(3,4-dimethylphenyl)-1H-pyrazol-5-yl)-5-methoxy-1H-benzo[d]imidazole (9n);
5,6-dichloro-2-(3-phenyl-1H-pyrazol-5-yl)-1H-benzo[d]imidazole (10a);
5,6-dichloro-2-(3-(4-methoxyphenyl)-1H-pyrazol-5-yl)-1H-benzo[d]imidazole (10b);
5,6-dichloro-2-(3-(3,4-dimethoxyphenyl)-1H-pyrazol-5-yl)-1H-benzo[d]imidazole (10c);
5,6-dichloro-2-(3-(3,5-dimethoxyphenyl)-1H-pyrazol-5-yl)-1H-benzo[d]imidazole (10d);
5,6-dichloro-2-(3-(2,4-dimethoxyphenyl)-1H-pyrazol-5-yl)-1H-benzo[d]imidazole (10e);
5,6-dichloro-2-(3-(3,4,5-trimethoxyphenyl)-1H-pyrazol-5-yl)-1H-benzo[d]imidazole (10f);
2-(3-(benzo[d][1,3]dioxol-5-yl)-1H-pyrazol-5-yl)-5,6-dichloro-1H-benzo[d]imidazole (10g);
5,6-dichloro-2-(3-(4-fluorophenyl)-1H-pyrazol-5-yl)-1H-benzo[d]imidazole (10h);
5,6-dichloro-2-(3-(3,4-difluorophenyl)-1H-pyrazol-5-yl)-1H-benzo[d]imidazole (10i);
5,6-dichloro-2-(3-(4-chlorophenyl)-1H-pyrazol-5-yl)-1H-benzo[d]imidazole (10j);
5,6-dichloro-2-(3-(3,4-dichlorophenyl)-1H-pyrazol-5-yl)-1H-benzo[d]imidazole (10k);
5,6-dichloro-2-(3-(2-fluoro-4-methoxyphenyl)-1H-pyrazol-5-yl)-1H-benzo[d]imidazole (10l);
5,6-dichloro-2-(3-p-tolyl-1H-pyrazol-5-yl)-1H-benzo[d]imidazole (10m);
5,6-dichloro-2-(3-(3,4-dimethylphenyl)-1H-pyrazol-5-yl)-1H-benzo[d]imidazole (10n);
2-(3-phenyl-1H-pyrazol-5-yl)-5-(trifluoromethyl)-1H-benzo[d]imidazole (11a);
2-(3-(4-methoxyphenyl)-1H-pyrazol-5-yl)-5-(trifluoromethyl)-1H-benzo[d]imidazole (11b);
2-(3-(3,4-dimethoxyphenyl)-1H-pyrazol-5-yl)-5-(trifluoromethyl)-1H-benzo[d]imidazole (11c);
2-(3-(3,5-dimethoxyphenyl)-1H-pyrazol-5-yl)-5-(trifluoromethyl)-1H-benzo[d]imidazole (11d);
2-(3-(2,4-dimethoxyphenyl)-1H-pyrazol-5-yl)-5-(trifluoromethyl)-1H-benzo[d]imidazole (11e);
5-(trifluoromethyl)-2-(3-(3,4,5-trimethoxyphenyl)-1H-pyrazol-5-yl)-1H-benzo[d]imidazole (11f);
2-(3-(benzo[d][1,3]dioxol-5-yl)-1H-pyrazol-5-yl)-5-(trifluoromethyl)-1H-benzo[d]imidazole (11g);
2-(3-(4-fluorophenyl)-1H-pyrazol-5-yl)-5-(trifluoromethyl)-1H-benzo[d]imidazole (11h);
2-(3-(3,4-difluorophenyl)-1H-pyrazol-5-yl)-5-(trifluoromethyl)-1H-benzo[d]imidazole (11f);
2-(3-(4-chlorophenyl)-1H-pyrazol-5-yl)-5-(trifluoromethyl)-1H-benzo[d]imidazole (11j);
2-(3-(3,4-dichlorophenyl)-1H-pyrazol-5-yl)-5-(trifluoromethyl)-1H-benzo[d]imidazole (11k);
2-(3-(2-fluoro-4-methoxyphenyl)-1H-pyrazol-5-yl)-5-(trifluoromethyl)-1H-benzo[d]imidazole (11l);
2-(3-p-tolyl-1H-pyrazol-5-yl)-5-(trifluoromethyl)-1H-benzo[d]imidazole (11m);
2-(3-(3,4-dimethylphenyl)-1H-pyrazol-5-yl)-5-(trifluoromethyl)-1H-benzo[d]imidazole (11n);
5-nitro-2-(3-phenyl-1H-pyrazol-5-yl)-1H-benzo[d]imidazole (12a);

2-(3-(4-methoxyphenyl)-1H-pyrazol-5-yl)-5-nitro-1H-benzo[d]imidazole (12b);
2-(3-(3,4-dimethoxyphenyl)-1H-pyrazol-5-yl)-5-nitro-1H-benzo[d]imidazole (12c);
2-(3-(3,5-dimethoxyphenyl)-1H-pyrazol-5-yl)-5-nitro-1H-benzo[d]imidazole (12d);
2-(3-(2,4-dimethoxyphenyl)-1H-pyrazol-5-yl)-5-nitro-1H-benzo[d]imidazole (12e);
5-nitro-2-(3-(3,4,5-trimethoxyphenyl)-1H-pyrazol-5-yl)-1H-benzo[d]imidazole (12f);
2-(3-(benzo[d][1,3]dioxol-5-yl)-1H-pyrazol-5-yl)-5-nitro-1H-benzo[d]imidazole (12g);
2-(3-(4-fluorophenyl)-1H-pyrazol-5-yl)-5-nitro-1H-benzo[d]imidazole (12h);
2-(3-(3,4-difluorophenyl)-1H-pyrazol-5-yl)-5-nitro-1H-benzo[d]imidazole (12i);
2-(3-(4-chlorophenyl)-1H-pyrazol-5-yl)-5-nitro-1H-benzo[d]imidazole (12j);
2-(3-(3,4-dichlorophenyl)-1H-pyrazol-5-yl)-5-nitro-1H-benzo[d]imidazole (12k);
2-(3-(2-fluoro-4-methoxyphenyl)-1H-pyrazol-5-yl)-5-nitro-1H-benzo[d]imidazole (12l);
5-nitro-2-(3-p-tolyl-1H-pyrazol-5-yl)-1H-benzo[d]imidazole (12m);
2-(3-(3,4-dimethylphenyl)-1H-pyrazol-5-yl)-5-nitro-1H-benzo[d]imidazole (12n);
5-chloro-6-fluoro-2-(3-phenyl-1H-pyrazol-5-yl)-1H-benzo[d]imidazole (13a);
5-chloro-6-fluoro-2-(3-(4-methoxyphenyl)-1H-pyrazol-5-yl)-1H-benzo[d]imidazole (13b);
5-chloro-2-(3-(3,4-dimethoxyphenyl)-1H-pyrazol-5-yl)-6-fluoro-1H-benzo[d]imidazole (13c);
5-chloro-2-(3-(3,5-dimethoxyphenyl)-1H-pyrazol-5-yl)-6-fluoro-1H-benzo[d]imidazole (13d);
5-chloro-2-(3-(2,4-dimethoxyphenyl)-1H-pyrazol-5-yl)-6-fluoro-1H-benzo[d]imidazole (13e);
5-chloro-6-fluoro-2-(3-(3,4,5-trimethoxyphenyl)-1H-pyrazol-5-yl)-1H-benzo[d]imidazole (13 f);
2-(3-(benzo[d][1,3]dioxol-5-yl)-1H-pyrazol-5-yl)-5-chloro-6-fluoro-1H-benzo[d]imidazole (13g);
5-chloro-6-fluoro-2-(3-(4-fluorophenyl)-1H-pyrazol-5-yl)-1H-benzo[d]imidazole (13h);
5-chloro-2-(3-(3,4-difluorophenyl)-1H-pyrazol-5-yl)-6-fluoro-1H-benzo[d]imidazole (13i);
5-chloro-2-(3-(4-chlorophenyl)-1H-pyrazol-5-yl)-6-fluoro-1H-benzo[d]imidazole (13j);
6-chloro-2-(3-(3,4-dichlorophenyl)-1H-pyrazol-5-yl)-5-fluoro-1H-benzo[d]imidazole (13k);
6-chloro-5-fluoro-2-(3-(2-fluoro-4-methoxyphenyl)-1H-pyrazol-5-yl)-1H-benzo[d]imidazole (13l);
6-chloro-5-fluoro-2-(3-p-tolyl-1H-pyrazol-5-yl)-1H-benzo[d]imidazole (13m);
6-chloro-2-(3-(3,4-dimethylphenyl)-1H-pyrazol-5-yl)-5-fluoro-1H-benzo[d]imidazole (13n);
6-bromo-2-(3-phenyl-1H-pyrazol-5-yl)-5-(trifluoromethyl)-1H-benzo[d]imidazole (14a);
6-bromo-2-(3-(4-methoxyphenyl)-1H-pyrazol-5-yl)-5-(trifluoromethyl)-1H-benzo[d]imidazole (14b);
6-bromo-2-(3-(3,4-dimethoxyphenyl)-1H-pyrazol-5-yl)-5-(trifluoromethyl)-1H-benzo[d]imidazole (14c);
6-bromo-2-(3-(3,5-dimethoxyphenyl)-1H-pyrazol-5-yl)-5-(trifluoromethyl)-1H-benzo[d]imidazole (14d);
6-bromo-2-(3-(2,4-dimethoxyphenyl)-1H-pyrazol-5-yl)-5-(trifluoromethyl)-1H-benzo[d]imidazole (14e);
6-bromo-5-(trifluoromethyl)-2-(3-(3,4,5-trimethoxyphenyl)-1H-pyrazol-5-yl)-1H-benzo[d]imidazole (14f);
2-(3-(benzo[d][1,3]dioxol-5-yl)-1H-pyrazol-5-yl)-6-bromo-5-(trifluoromethyl)-1H-benzo[d]imidazole (14g);
6-bromo-2-(3-(4-fluorophenyl)-1H-pyrazol-5-yl)-5-(trifluoromethyl)-1H-benzo[d]imidazole (14h);
6-bromo-2-(3-(3,4-difluorophenyl)-1H-pyrazol-5-yl)-5-(trifluoromethyl)-1H-benzo[d]imidazole (14i);
6-bromo-2-(3-(4-chlorophenyl)-1H-pyrazol-5-yl)-5-(trifluoromethyl)-1H-benzo[d]imidazole (14j);
6-bromo-2-(3-(3,4-dichlorophenyl)-1H-pyrazol-5-yl)-5-(trifluoromethyl)-1H-benzo[d]imidazole (14k);
6-bromo-2-(3-(2-fluoro-4-methoxyphenyl)-1H-pyrazol-5-yl)-5-(trifluoromethyl)-1H-benzo[d]imidazole (14l);
6-bromo-2-(3-p-tolyl-1H-pyrazol-5-yl)-5-(trifluoromethyl)-1H-benzo[d]imidazole (14m); and
6-bromo-2-(3-(3,4-dimethylphenyl)-1H-pyrazol-5-yl)-5-(trifluoromethyl)-1H-benzo[d]imidazole (14n).

In certain aspects, the present invention provides at least one compound having anticancerous activity, wherein the one or more compounds comprise a pyrazole-benzimidazole conjugate of Formula A.

In certain other aspects of the present invention, the one or more compounds comprising a pyrazole-benzimidazole conjugate of Formula A possess anticancer activity against cell lines selected from the group consisting of leukemia, non-small cell lung cancer, colon cancer, CNS cancer, melanoma, ovarian cancer, renal cancer, prostate cancer and breast cancer.

According to certain aspects, the present invention also provides a process for the preparation of pyrazole linked benzimidazole conjugates of Formulae A, the process comprising:

(a) reacting at least one 3-aryl-1H-pyrazole-5-carbaldehyde of formula (5a-n).

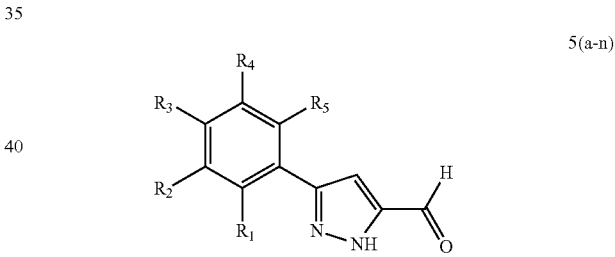

5(a-n)

wherein $R_1$, $R_2$, $R_3$, $R_4$, $R_5$=[H, Cl, F, $CH_3$, $OCH_3$, 3,4($OCH_2O$)]

with at least one compound selected from a group consisting of formulae 1, 2, 3, 4, 5, 6, 7, 8, 9 and 10:

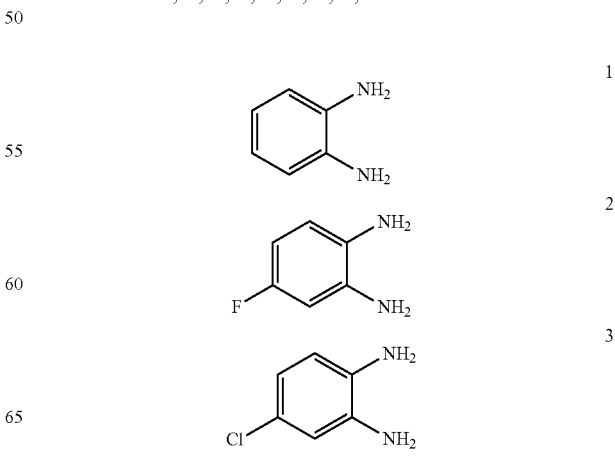

-continued

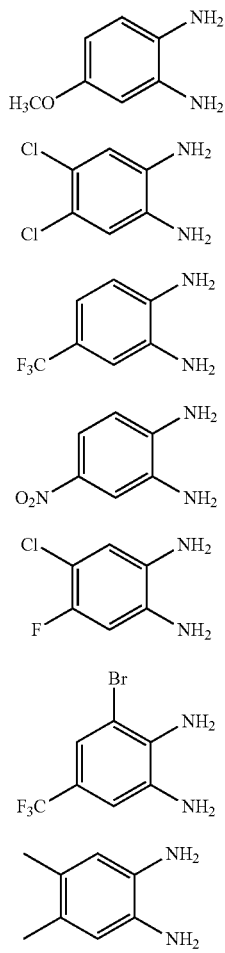

in a protic water miscible solvent, such as ethanol or methanol, in the presence of catalyst selected from Na2S2O5 at a temperature in the range of 85° C. to 90° C. for a time period in the range of about 3 hours to about 4 hours;

(b) evaporating the solvent under vacuum and extracting it with water immiscible solvent;

(c) washing combined layers with water;

(d) drying the washed combined layers over anhydrous Na2SO4;

(e) evaporating the solvent to obtain crude product; and (f) purifying the crude product with column chromatography to obtain the desired products of formulae A.

In an embodiment of the present invention, the water immiscible solvent may be selected from the group consisting of ethyl acetate, chloroform, dichloromethane and combinations thereof.

The above summary of the various representative aspects and embodiments of the present invention is not intended to describe each illustrated aspect or embodiment or every implementation of the present invention. Rather, the aspects and embodiments are chosen and described so that others skilled in the art can appreciate and understand the principles and practices of the present invention.

DETAILED DESCRIPTION OF THE PRESENT INVENTION

The present invention is directed at pyrazole-benzimidazole conjugates of Formula A:

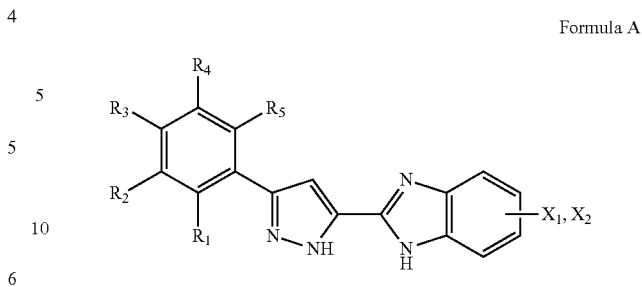

Formula A wherein substituent $R_1$ in Formula A is chosen from H, Cl, F, $CH_3$, $OCH_3$ and $3,4(OCH_2O)$;

wherein substituent $R_2$ in Formula A is chosen from H, Cl, F, $CH_3$, $OCH_3$ and $3,4(OCH_2O)$;

wherein substituent $R_3$ in Formula A is chosen from H, Cl, F, $CH_3$, $OCH_3$ and $3,4(OCH_2O)$;

wherein substituent $R_4$ in Formula A is chosen from H, Cl, F, $CH_3$, $OCH_3$ and $3,4(OCH_2O)$;

wherein substituent $R_5$ in Formula A is chosen from H, Cl, F, $CH_3$, $OCH_3$ and $3,4(OCH_2O)$;

wherein substituent $X_1$ in Formula A is chosen from H, Br, Cl, F, $CH_3$, $OCH_3$, $NO_2$ and $CF_3$; and wherein substituent $X_2$ in Formula A is chosen from H, Br, Cl, F, $CH_3$, and $CF_3$.

The synthesis of pyrazole-benzimidazole conjugates of Formula A are outlined in Scheme 1:

Scheme 1

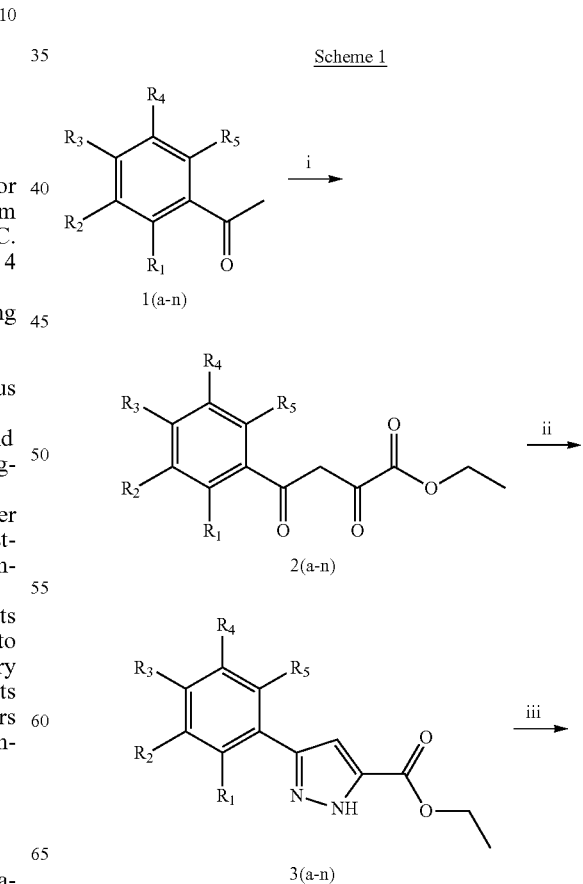

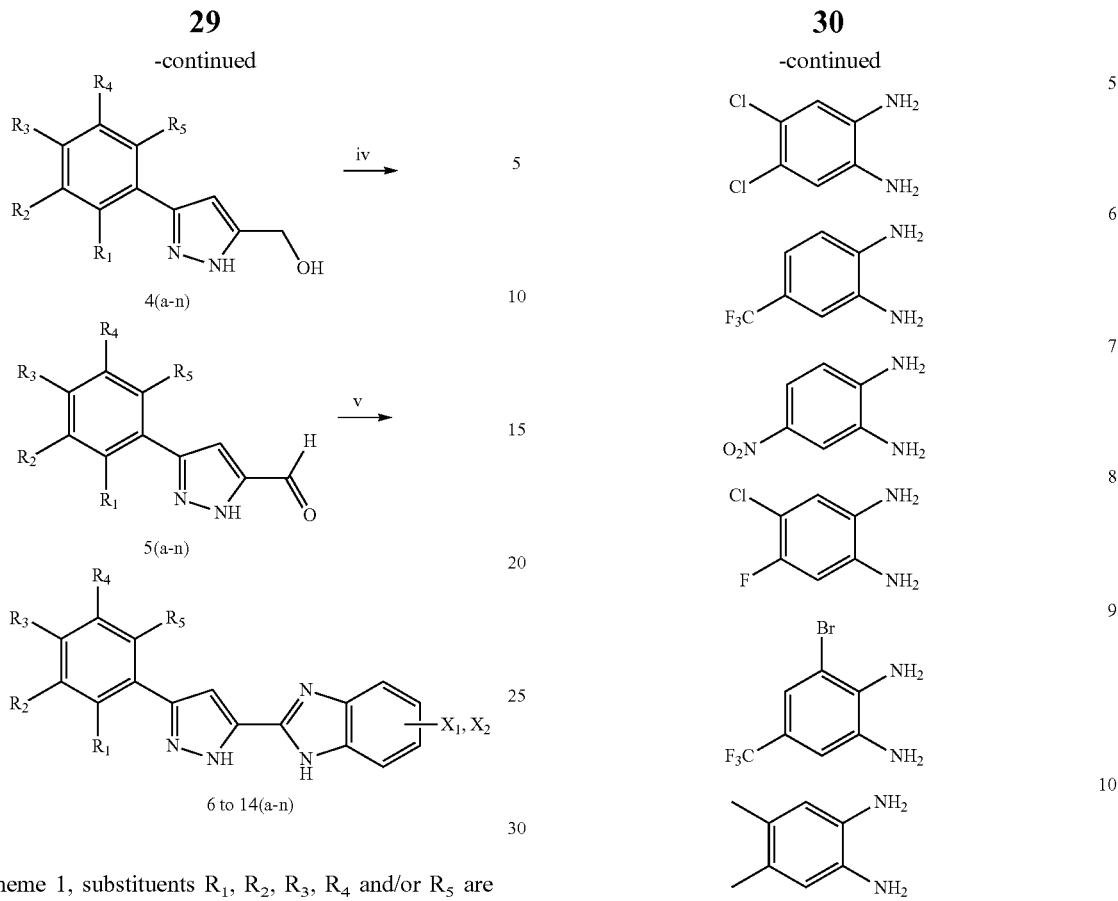

In Scheme 1, substituents $R_1$, $R_2$, $R_3$, $R_4$ and/or $R_5$ are chosen from H, Cl, F, $CH_3$, $OCH_3$ and 3,4($OCH_2O$). Also, substituent $X_1$ of the pyrazole-benzimidazole conjugate is chosen from H, Br, Cl, F, $CH_3$, $OCH_3$, $NO_2$ and $CF_3$, and substituent $X_2$ of the pyrazole-benzimidazole conjugate is chosen from H, Br, Cl, F, $CH_3$, and $CF_3$.

The final step in Scheme 1 can comprise oxidative cyclization of o-phenylenediamines of formulae 1, 2, 3, 4, 5, 6, 7, 8, 9, 10 and 3-phenyl-1H-pyrazole-5-carbaldehydes of formulae 5(a-n) with sodium metabisulphite in ethanol/methanol solvent system at a temperature of about 85° C. for about 3 hours to about 4 hours.

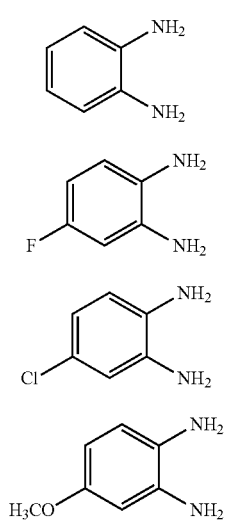

wherein substituents $R_1$, $R_2$, $R_3$, $R_4$ and/or $R_5$ in formulae 5(a-n) are chosen from H, Cl, F, $CH_3$, $OCH_3$ and 3,4 ($OCH_2O$).

According to certain aspects of the present invention, the reagents, conditions and (yields) of steps (i) to (v) of Scheme 1 are:

(i) NaOEt, EtOH for about 4h at a temperature of about 0° C. to about 21° C. (85-90%);

(ii) NH2-NH2.2HCl, EtOH at about 3 h, reflux, (72-79%);

(iii) LiAlH4, THF, for about 1 to about 2 hours at a temperature of about 0° C. to about 21° C., (70-80%);

(iv) IBX, dry DMSO, at about 1 hour at about room temperate, (80-90%); and (v) Na2S2O5, EtOH, o-phenylenediamines, at about 3 hours to about 4 hours at a about room temperature (70-80%).

The key intermediates 3-substituted phenyl-1H-pyrazole-5-carbaldehydes having formulae 5(a-n) in Scheme 1 can be prepared in four sequential steps. Initially substituted acetophenones 1(a-n) reacted with diethyl oxalate in the presence of sodium ethanolate in ethanol yielded ethyl 2,4-dioxo-4-(substituted phenyl)butanoates 2(a-n). This was further cyclised with NH2-NH2.2HCl in ethanol to produce ethyl 3-substituted phenyl-1H-pyrazole-5-carboxylates 3(a-n) in good yields. The obtained carboxylates were reduced to (3-substituted phenyl-1H-pyrazol-5-yl) methanols 4(a-n) by LiAlH4/THF. These were selectively oxidized to 3-substituted phenyl-1H-pyrazole-5-carbaldehydes by IBX in DMSO.

Each 3-substituted phenyl-1H-pyrazole-5-carbaldehydes (5a-n) (1.0 mmol) were added to substituted o-phenylenediamines (formulae 1-10) (1.0 mmol) in ethanol (10 mL). A catalytic amount of Na2S2O5 (5 mg) was also charged to the reaction mixture and stirred at a temperature of 85° C. for 3-4 h. The reaction progress was monitored by TLC. After completion of reaction, the reaction mixture was cooled to room temperature with the addition of water (100 mL) followed by extraction with ethyl acetate (3×30 mL). The organic layers were washed with water, brine solution and dried over anhydrous Na2SO4. Evaporation of the solvent under vacuum yielded the crude product that was further purified by column chromatography using ethyl acetate/hexane solvent system.

In particular, the pyrazole-benzimidazole conjugates of Formula A prepared by the process outlined in Scheme 1 can be chosen from 2-(3-phenyl-1H-pyrazol-5-yl)-substituted-1H-benzo[d]imidazoles (formulae 6a-14a):

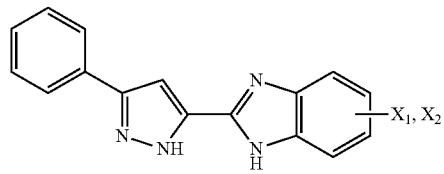
(6a-14a)

2-(3-(4-methoxyphenyl)-1H-pyrazol-5-yl)-substituted-1H-benzo[d]imidazoles (formulae 6b-14b)

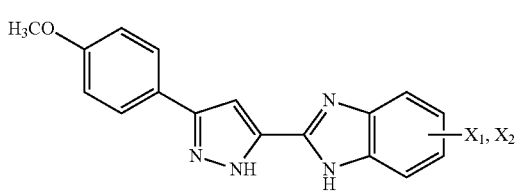
(6d-14b)

2-(3-(3,4-dimethoxyphenyl)-1H-pyrazol-5-yl)-substituted-1H-benzo[d]imidazoles (formulae 6c-14c)

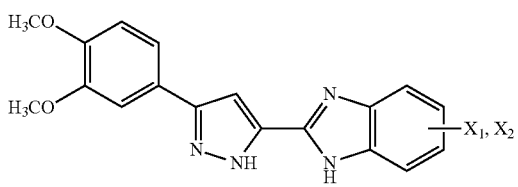
(6c-14c)

2-(3-(3,5-dimethoxyphenyl)-1H-pyrazol-5-yl)-substituted-1H-benzo[d]imidazoles (formulae 6d-14d)

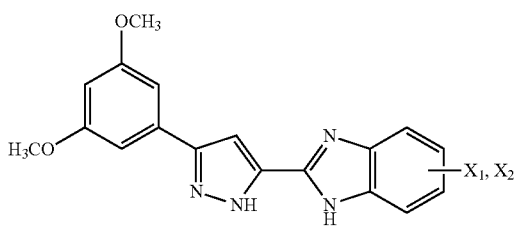
(6d-14d)

2-(3-(2,4-dimethoxyphenyl)-1H-pyrazol-5-yl)-substituted-1H-benzo[d]imidazoles (formulae 6e-14e)

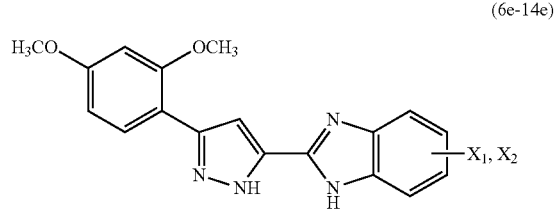
(6e-14e)

2-(3-(3,4,5-trimethoxyphenyl)-1H-pyrazol-5-yl)-substituted-1H-benzo[d]imidazoles (formulae 6f-14f)

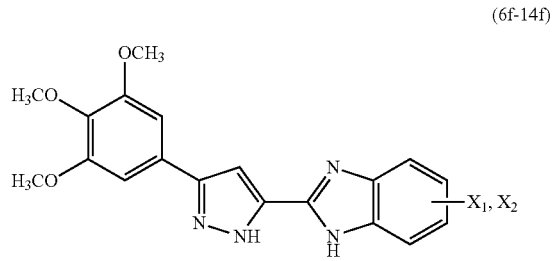
(6f-14f)

2-(3-(benzo[d][1,3]dioxol-5-yl)-1H-pyrazol-5-yl)-substituted-1H-benzo[d]imidazoles (formulae 6g-14g)

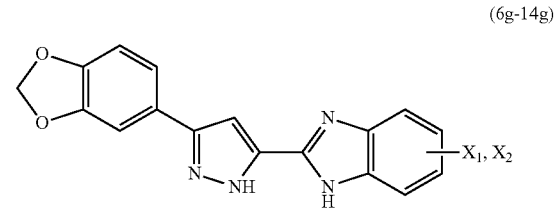
(6g-14g)

2-(3-(4-fluorophenyl)-1H-pyrazol-5-yl)-substituted-1H-benzo[d]imidazoles (formulae 6h-14h)

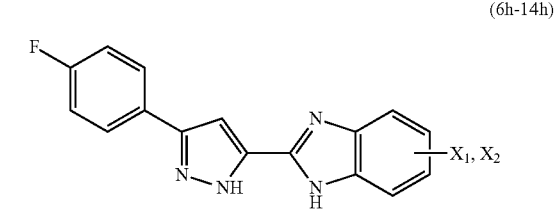
(6h-14h)

2-(3-(3,4-difluorophenyl)-1H-pyrazol-5-yl)-substituted-1H-benzo[d]imidazoles (formulae 6i-14i)

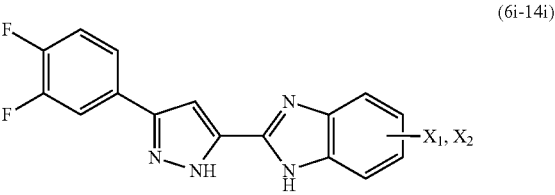
(6i-14i)

2-(3-(4-chlorophenyl)-1H-pyrazol-5-yl)-substituted-1H-benzo[d]imidazoles (formulae 6j-14j)

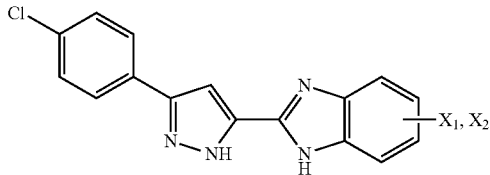

(6j-14j)

2-(3-(3,4-dichlorophenyl)-1H-pyrazol-5-yl)-substituted-1H-benzo[d]imidazoles (formulae 6k-14k)

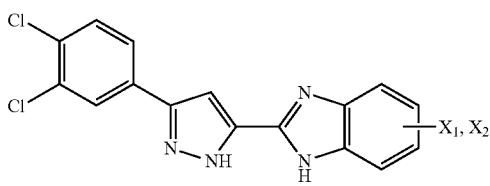

(6k-14k)

2-(3-(2-fluoro-4-methoxyphenyl)-1H-pyrazol-5-yl)-substituted-1H-benzo[d]imidazoles (formulae 6l-14l)

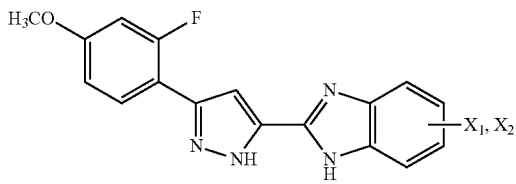

(6l-14l)

2-(3-p-tolyl-1H-pyrazol-5-yl)-substituted-1H-benzo[d]imidazoles (formulae 6m-14m)

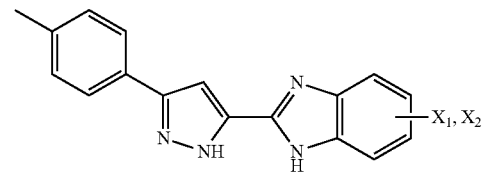

(6m-14m)

2-(3-(3,4-dimethylphenyl)-1H-pyrazol-5-yl)-substituted-1H-benzo[d]imidazoles (formulae 6n-14n)

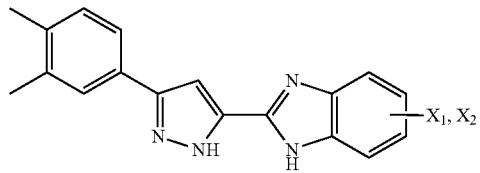

(6n-14n)

wherein the $X_1$ substituent in the foregoing formulae is chosen from H, Br, Cl, F, $CH_3$, $OCH_3$, $NO_2$ and $CF_3$, and the $X_2$ substituent in the foregoing formulae is chosen from H, Br, Cl, F, $CH_3$, and $CF_3$.

In certain aspects, the pyrazole linked benzimidazole conjugates of the present invention are represented by the group of the following compounds:

2-(3-phenyl-1H-pyrazol-5-yl)-1H-benzo[d]imidazole having formula (6a);
2-(3-(4-methoxyphenyl)-1H-pyrazol-5-yl)-1H-benzo[d]imidazole having formula (6b);
2-(3-(3,4-dimethoxyphenyl)-1H-pyrazol-5-yl)-1H-benzo[d]imidazole having formula (6c);
2-(3-(3,5-dimethoxyphenyl)-1H-pyrazol-5-yl)-1H-benzo[d]imidazole having formula (6d);
2-(3-(2,4-dimethoxyphenyl)-1H-pyrazol-5-yl)-1H-benzo[d]imidazole having formula (6e);
2-(3-(3,4,5-trimethoxyphenyl)-1H-pyrazol-5-yl)-1H-benzo[d]imidazole having formula (6f);
2-(3-(benzo[d][1,3]dioxol-5-yl)-1H-pyrazol-5-yl)-1H-benzo[d]imidazole having formula (6g);
2-(3-(4-fluorophenyl)-1H-pyrazol-5-yl)-1H-benzo[d]imidazole having formula (6h);
2-(3-(3,4-difluorophenyl)-1H-pyrazol-5-yl)-1H-benzo[d]imidazole having formula (6i);
2-(3-(4-chlorophenyl)-1H-pyrazol-5-yl)-1H-benzo[d]imidazole having formula (6j);
2-(3-(3,4-dichlorophenyl)-1H-pyrazol-5-yl)-1H-benzo[d]imidazole having formula (6k);
2-(3-(2-fluoro-4-methoxyphenyl)-1H-pyrazol-5-yl)-1H-benzo[d]imidazole having formula (6l);
2-(3-p-tolyl-1H-pyrazol-5-yl)-1H-benzo[d]imidazole having formula (6m);
2-(3-(3,4-dimethylphenyl)-1H-pyrazol-5-yl)-1H-benzo[d]imidazole having formula (6n);
5-fluoro-2-(3-phenyl-1H-pyrazol-5-yl)-1H-benzo[d]imidazole having formula (7a);
5-fluoro-2-(3-(4-methoxyphenyl)-1H-pyrazol-5-yl)-1H-benzo[d]imidazole having formula (7b);
2-(3-(3,4-dimethoxyphenyl)-1H-pyrazol-5-yl)-5-fluoro-1H-benzo[d]imidazole having formula (7c);
2-(3-(3,5-dimethoxyphenyl)-1H-pyrazol-5-yl)-5-fluoro-1H-benzo[d]imidazole having formula (7d);
2-(3-(2,4-dimethoxyphenyl)-1H-pyrazol-5-yl)-5-fluoro-1H-benzo[d]imidazole having formula (7e);
5-fluoro-2-(3-(3,4,5-trimethoxyphenyl)-1H-pyrazol-5-yl)-1H-benzo[d]imidazole having formula (7f);
2-(3-(benzo[d][1,3]dioxol-5-yl)-1H-pyrazol-5-yl)-5-fluoro-1H-benzo[d]imidazole having formula (7g);
5-fluoro-2-(3-(4-fluorophenyl)-1H-pyrazol-5-yl)-1H-benzo[d]imidazole having formula (7h);
2-(3-(3,4-difluorophenyl)-1H-pyrazol-5-yl)-5-fluoro-1H-benzo[d]imidazole having formula (7i);
2-(3-(4-chlorophenyl)-1H-pyrazol-5-yl)-5-fluoro-1H-benzo[d]imidazole having formula (7j);
2-(3-(3,4-dichlorophenyl)-1H-pyrazol-5-yl)-5-fluoro-1H-benzo[d]imidazole having formula (7k);
5-fluoro-2-(3-(2-fluoro-4-methoxyphenyl)-1H-pyrazol-5-yl)-1H-benzo[d]imidazole having formula (7l);
5-fluoro-2-(3-p-tolyl-1H-pyrazol-5-yl)-1H-benzo[d]imidazole having formula (7m);
2-(3-(3,4-dimethylphenyl)-1H-pyrazol-5-yl)-5-fluoro-1H-benzo[d]imidazole having formula (7n);
5-chloro-2-(3-phenyl-1H-pyrazol-5-yl)-1H-benzo[d]imidazole having formula (8a);
5-chloro-2-(3-(4-methoxyphenyl)-1H-pyrazol-5-yl)-1H-benzo[d]imidazole having formula (8b);

5-chloro-2-(3-(3,4-dimethoxyphenyl)-1H-pyrazol-5-yl)-1H-benzo[d]imidazole having formula (8c);
5-chloro-2-(3-(3,5-dimethoxyphenyl)-1H-pyrazol-5-yl)-1H-benzo[d]imidazole having formula (8d);
5-chloro-2-(3-(2,4-dimethoxyphenyl)-1H-pyrazol-5-yl)-1H-benzo[d]imidazole having formula (8e);
5-chloro-2-(3-(3,4,5-trimethoxyphenyl)-1H-pyrazol-5-yl)-1H-benzo[d]imidazole having formula (8f);
2-(3-(benzo[d][1,3]dioxol-5-yl)-1H-pyrazol-5-yl)-5-chloro-1H-benzo[d]imidazole having formula (8g);
5-chloro-2-(3-(4-fluorophenyl)-1H-pyrazol-5-yl)-1H-benzo[d]imidazole having formula (8h);
5-chloro-2-(3-(3,4-difluorophenyl)-1H-pyrazol-5-yl)-1H-benzo[d]imidazole having formula (8i);
5-chloro-2-(3-(4-chlorophenyl)-1H-pyrazol-5-yl)-1H-benzo[d]imidazole having formula (8j);
5-chloro-2-(3-(3,4-dichlorophenyl)-1H-pyrazol-5-yl)-1H-benzo[d]imidazole having formula (8k);
5-chloro-2-(3-(2-fluoro-4-methoxyphenyl)-1H-pyrazol-5-yl)-1H-benzo[d]imidazole having formula (8l);
5-chloro-2-(3-p-tolyl-1H-pyrazol-5-yl)-1H-benzo[d]imidazole having formula (8m);
5-chloro-2-(3-(3,4-dimethylphenyl)-1H-pyrazol-5-yl)-1H-benzo[d]imidazole having formula (8n);
5-methoxy-2-(3-phenyl-1H-pyrazol-5-yl)-1H-benzo[d]imidazole having formula (9a);
5-methoxy-2-(3-(4-methoxyphenyl)-1H-pyrazol-5-yl)-1H-benzo[d]imidazole having formula (9b);
2-(3-(3,4-dimethoxyphenyl)-1H-pyrazol-5-yl)-5-methoxy-1H-benzo[d]imidazole having formula (9c);
2-(3-(3,5-dimethoxyphenyl)-1H-pyrazol-5-yl)-5-methoxy-1H-benzo[d]imidazole having formula (9d);
2-(3-(2,4-dimethoxyphenyl)-1H-pyrazol-5-yl)-5-methoxy-1H-benzo[d]imidazole having formula (9e);
5-methoxy-2-(3-(3,4,5-trimethoxyphenyl)-1H-pyrazol-5-yl)-1H-benzo[d]imidazole having formula (9f);
2-(3-(benzo[d][1,3]dioxol-5-yl)-1H-pyrazol-5-yl)-5-methoxy-1H-benzo[d]imidazole having formula (9g);
2-(3-(4-fluorophenyl)-1H-pyrazol-5-yl)-5-methoxy-1H-benzo[d]imidazole having formula (9h);
2-(3-(3,4-difluorophenyl)-1H-pyrazol-5-yl)-5-methoxy-1H-benzo[d]imidazole having formula (9i);
2-(3-(4-chlorophenyl)-1H-pyrazol-5-yl)-5-methoxy-1H-benzo[d]imidazole having formula (9j);
2-(3-(3,4-dichlorophenyl)-1H-pyrazol-5-yl)-5-methoxy-1H-benzo[d]imidazole having formula (9k);
2-(3-(2-fluoro-4-methoxyphenyl)-1H-pyrazol-5-yl)-5-methoxy-1H-benzo[d]imidazole having formula (9l);
5-methoxy-2-(3-p-tolyl-1H-pyrazol-5-yl)-1H-benzo[d]imidazole having formula (9m);
2-(3-(3,4-dimethylphenyl)-1H-pyrazol-5-yl)-5-methoxy-1H-benzo[d]imidazole having formula (9n);
5,6-dichloro-2-(3-phenyl-1H-pyrazol-5-yl)-1H-benzo[d]imidazole having formula (10a);
5,6-dichloro-2-(3-(4-methoxyphenyl)-1H-pyrazol-5-yl)-1H-benzo[d]imidazole having formula (10b);
5,6-dichloro-2-(3-(3,4-dimethoxyphenyl)-1H-pyrazol-5-yl)-1H-benzo[d]imidazole having formula (10c);
5,6-dichloro-2-(3-(3,5-dimethoxyphenyl)-1H-pyrazol-5-yl)-1H-benzo[d]imidazole having formula (10d);
5,6-dichloro-2-(3-(2,4-dimethoxyphenyl)-1H-pyrazol-5-yl)-1H-benzo[d]imidazole having formula (10e);
5,6-dichloro-2-(3-(3,4,5-trimethoxyphenyl)-1H-pyrazol-5-yl)-1H-benzo[d]imidazole having formula (10f);
2-(3-(benzo[d][1,3]dioxol-5-yl)-1H-pyrazol-5-yl)-5,6-dichloro-1H-benzo[d]imidazole having formula (10g);
5,6-dichloro-2-(3-(4-fluorophenyl)-1H-pyrazol-5-yl)-1H-benzo[d]imidazole having formula (10h);
5,6-dichloro-2-(3-(3,4-difluorophenyl)-1H-pyrazol-5-yl)-1H-benzo[d]imidazole having formula (10i);
5,6-dichloro-2-(3-(4-chlorophenyl)-1H-pyrazol-5-yl)-1H-benzo[d]imidazole having formula (10j);
5,6-dichloro-2-(3-(3,4-dichlorophenyl)-1H-pyrazol-5-yl)-1H-benzo[d]imidazole having formula (10k);
5,6-dichloro-2-(3-(2-fluoro-4-methoxyphenyl)-1H-pyrazol-5-yl)-1H-benzo[d]imidazole having formula (10l);
5,6-dichloro-2-(3-p-tolyl-1H-pyrazol-5-yl)-1H-benzo[d]imidazole having formula (10m);
5,6-dichloro-2-(3-(3,4-dimethylphenyl)-1H-pyrazol-5-yl)-1H-benzo[d]imidazole having formula (10n);
2-(3-phenyl-1H-pyrazol-5-yl)-5-(trifluoromethyl)-1H-benzo[d]imidazole having formula (11a);
2-(3-(4-methoxyphenyl)-1H-pyrazol-5-yl)-5-(trifluoromethyl)-1H-benzo[d]imidazole having formula (11b);
2-(3-(3,4-dimethoxyphenyl)-1H-pyrazol-5-yl)-5-(trifluoromethyl)-1H-benzo[d]imidazole having formula (11c);
2-(3-(3,5-dimethoxyphenyl)-1H-pyrazol-5-yl)-5-(trifluoromethyl)-1H-benzo[d]imidazole having formula (11d);
2-(3-(2,4-dimethoxyphenyl)-1H-pyrazol-5-yl)-5-(trifluoromethyl)-1H-benzo[d]imidazole having formula (11e);
5-(trifluoromethyl)-2-(3-(3,4,5-trimethoxyphenyl)-1H-pyrazol-5-yl)-1H-benzo[d]imidazole having formula (11f);
2-(3-(benzo[d][1,3]dioxol-5-yl)-1H-pyrazol-5-yl)-5-(trifluoromethyl)-1H-benzo[d]imidazole having formula (11g);
2-(3-(4-fluorophenyl)-1H-pyrazol-5-yl)-5-(trifluoromethyl)-1H-benzo[d]imidazole having formula (11h);
2-(3-(3,4-difluorophenyl)-1H-pyrazol-5-yl)-5-(trifluoromethyl)-1H-benzo[d]imidazole having formula (11i);
2-(3-(4-chlorophenyl)-1H-pyrazol-5-yl)-5-(trifluoromethyl)-1H-benzo[d]imidazole having formula (11j);
2-(3-(3,4-dichlorophenyl)-1H-pyrazol-5-yl)-5-(trifluoromethyl)-1H-benzo[d]imidazole having formula (11k);
2-(3-(2-fluoro-4-methoxyphenyl)-1H-pyrazol-5-yl)-5-(trifluoromethyl)-1H-benzo[d]imidazole having formula (11l);
2-(3-p-tolyl-1H-pyrazol-5-yl)-5-(trifluoromethyl)-1H-benzo[d]imidazole having formula (11m);
2-(3-(3,4-dimethylphenyl)-1H-pyrazol-5-yl)-5-(trifluoromethyl)-1H-benzo[d]imidazole having formula (11n);
5-nitro-2-(3-phenyl-1H-pyrazol-5-yl)-1H-benzo[d]imidazole having formula (12a);
2-(3-(4-methoxyphenyl)-1H-pyrazol-5-yl)-5-nitro-1H-benzo[d]imidazole having formula (12b);
2-(3-(3,4-dimethoxyphenyl)-1H-pyrazol-5-yl)-5-nitro-1H-benzo[d]imidazole having formula (12c);
2-(3-(3,5-dimethoxyphenyl)-1H-pyrazol-5-yl)-5-nitro-1H-benzo[d]imidazole having formula (12d);
2-(3-(2,4-dimethoxyphenyl)-1H-pyrazol-5-yl)-5-nitro-1H-benzo[d]imidazole having formula (12e);
5-nitro-2-(3-(3,4,5-trimethoxyphenyl)-1H-pyrazol-5-yl)-1H-benzo[d]imidazole having formula (12f);
2-(3-(benzo[d][1,3]dioxol-5-yl)-1H-pyrazol-5-yl)-5-nitro-1H-benzo[d]imidazole having formula (12g);
2-(3-(4-fluorophenyl)-1H-pyrazol-5-yl)-5-nitro-1H-benzo[d]imidazole having formula (12h);
2-(3-(3,4-difluorophenyl)-1H-pyrazol-5-yl)-5-nitro-1H-benzo[d]imidazole having formula (12i);
2-(3-(4-chlorophenyl)-1H-pyrazol-5-yl)-5-nitro-1H-benzo[d]imidazole having formula (12j);
2-(3-(3,4-dichlorophenyl)-1H-pyrazol-5-yl)-5-nitro-1H-benzo[d]imidazole having formula (12k);

2-(3-(2-fluoro-4-methoxyphenyl)-1H-pyrazol-5-yl)-5-nitro-1H-benzo[d]imidazole having formula (12l);

5-nitro-2-(3-p-tolyl-1H-pyrazol-5-yl)-1H-benzo[d]imidazole having formula (12m);

2-(3-(3,4-dimethylphenyl)-1H-pyrazol-5-yl)-5-nitro-1H-benzo[d]imidazole having formula (12n);

5-chloro-6-fluoro-2-(3-phenyl-1H-pyrazol-5-yl)-1H-benzo[d]imidazole having formula (13a);

5-chloro-6-fluoro-2-(3-(4-methoxyphenyl)-1H-pyrazol-5-yl)-1H-benzo[d]imidazole having formula (13b);

5-chloro-2-(3-(3,4-dimethoxyphenyl)-1H-pyrazol-5-yl)-6-fluoro-1H-benzo[d]imidazole having formula (13c);

5-chloro-2-(3-(3,5-dimethoxyphenyl)-1H-pyrazol-5-yl)-6-fluoro-1H-benzo[d]imidazole having formula (13d);

5-chloro-2-(3-(2,4-dimethoxyphenyl)-1H-pyrazol-5-yl)-6-fluoro-1H-benzo[d]imidazole having formula (13e);

5-chloro-6-fluoro-2-(3-(3,4,5-trimethoxyphenyl)-1H-pyrazol-5-yl)-1H-benzo[d]imidazole having formula (13f);

2-(3-(benzo[d][1,3]dioxol-5-yl)-1H-pyrazol-5-yl)-5-chloro-6-fluoro-1H-benzo[d]imidazole having formula (13g);

5-chloro-6-fluoro-2-(3-(4-fluorophenyl)-1H-pyrazol-5-yl)-1H-benzo[d]imidazole having formula (13h);

5-chloro-2-(3-(3,4-difluorophenyl)-1H-pyrazol-5-yl)-6-fluoro-1H-benzo[d]imidazole having formula (13i);

5-chloro-2-(3-(4-chlorophenyl)-1H-pyrazol-5-yl)-6-fluoro-1H-benzo[d]imidazole having formula (13j);

6-chloro-2-(3-(3,4-dichlorophenyl)-1H-pyrazol-5-yl)-5-fluoro-1H-benzo[d]imidazole having formula (13k);

6-chloro-5-fluoro-2-(3-(2-fluoro-4-methoxyphenyl)-1H-pyrazol-5-yl)-1H-benzo[d]imidazole having formula (13l);

6-chloro-5-fluoro-2-(3-p-tolyl-1H-pyrazol-5-yl)-1H-benzo[d]imidazole having formula (13m);

6-chloro-2-(3-(3,4-dimethylphenyl)-1H-pyrazol-5-yl)-5-fluoro-1H-benzo[d]imidazole having formula (13n);

6-bromo-2-(3-phenyl-1H-pyrazol-5-yl)-5-(trifluoromethyl)-1H-benzo[d]imidazole having formula (14a);

6-bromo-2-(3-(4-methoxyphenyl)-1H-pyrazol-5-yl)-5-(trifluoromethyl)-1H-benzo[d]imidazole having formula (14b);

6-bromo-2-(3-(3,4-dimethoxyphenyl)-1H-pyrazol-5-yl)-5-(trifluoromethyl)-1H-benzo[d]imidazole having formula (14c);

6-bromo-2-(3-(3,5-dimethoxyphenyl)-1H-pyrazol-5-yl)-5-(trifluoromethyl)-1H-benzo[d]imidazole having formula (14d);

6-bromo-2-(3-(2,4-dimethoxyphenyl)-1H-pyrazol-5-yl)-5-(trifluoromethyl)-1H-benzo[d]imidazole having formula (14e);

6-bromo-5-(trifluoromethyl)-2-(3-(3,4,5-trimethoxyphenyl)-1H-pyrazol-5-yl)-1H-benzo[d]imidazole having formula (14f);

2-(3-(benzo[d][1,3]dioxol-5-yl)-1H-pyrazol-5-yl)-6-bromo-5-(trifluoromethyl)-1H-benzo[d]imidazole having formula (14g);

6-bromo-2-(3-(4-fluorophenyl)-1H-pyrazol-5-yl)-5-(trifluoromethyl)-1H-benzo[d]imidazole having formula (14h);

6-bromo-2-(3-(3,4-difluorophenyl)-1H-pyrazol-5-yl)-5-(trifluoromethyl)-1H-benzo[d]imidazole having formula (14i);

6-bromo-2-(3-(4-chlorophenyl)-1H-pyrazol-5-yl)-5-(trifluoromethyl)-1H-benzo[d]imidazole having formula (14j);

6-bromo-2-(3-(3,4-dichlorophenyl)-1H-pyrazol-5-yl)-5-(trifluoromethyl)-1H-benzo[d]imidazole having formula (14k);

6-bromo-2-(3-(2-fluoro-4-methoxyphenyl)-1H-pyrazol-5-yl)-5-(trifluoromethyl)-1H-benzo[d]imidazole having formula (14l);

6-bromo-2-(3-p-tolyl-1H-pyrazol-5-yl)-5-(trifluoromethyl)-1H-benzo[d]imidazole having formula (14m); and 6-bromo-2-(3-(3,4-dimethylphenyl)-1H-pyrazol-5-yl)-5-(trifluoromethyl)-1H-benzo[d]imidazole having formula (14n);

wherein the representative structures of the foregoing are:

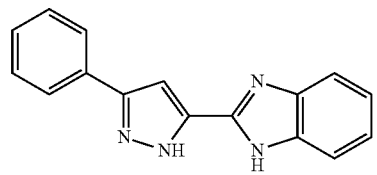

(6a)

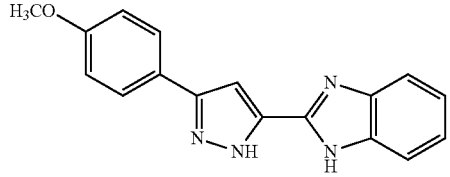

(6b)

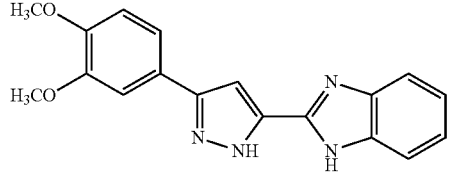

(6c)

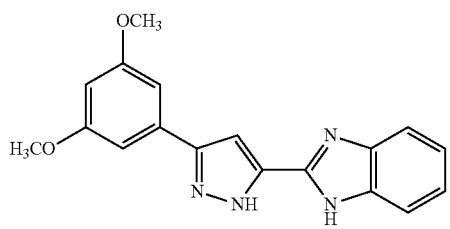

(6d)

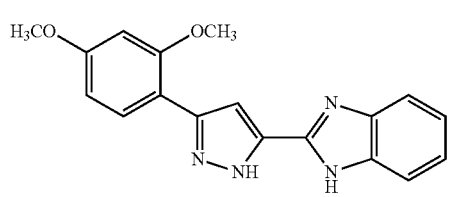

(6e)

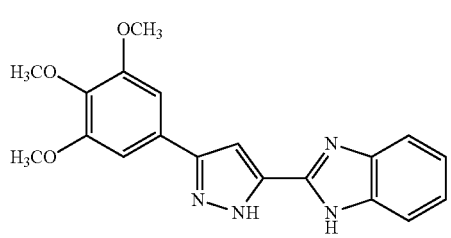

(6f)

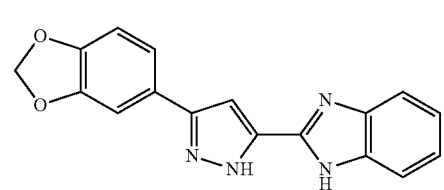

(6g)

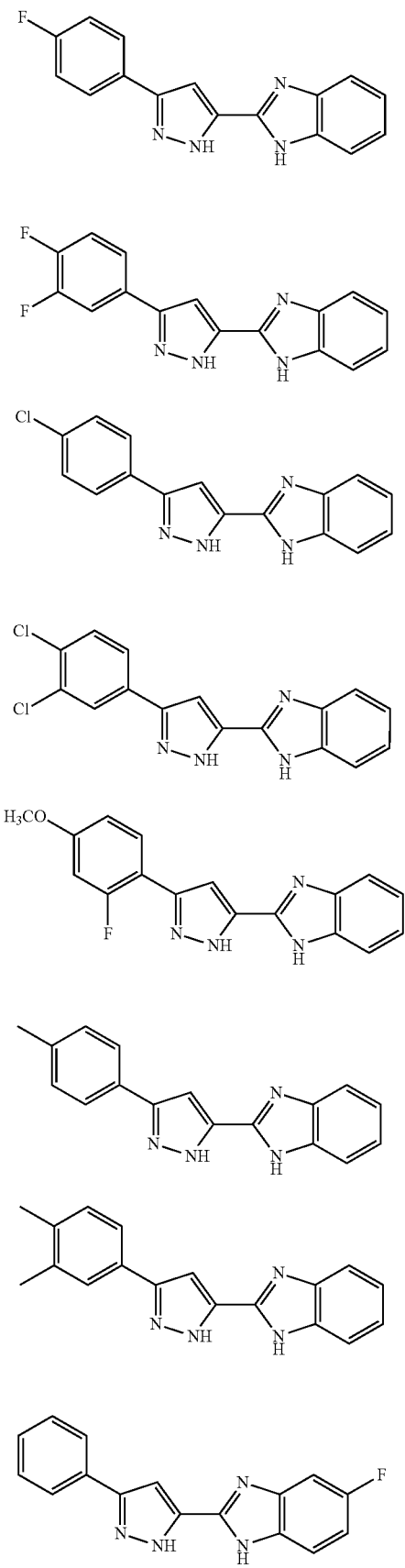
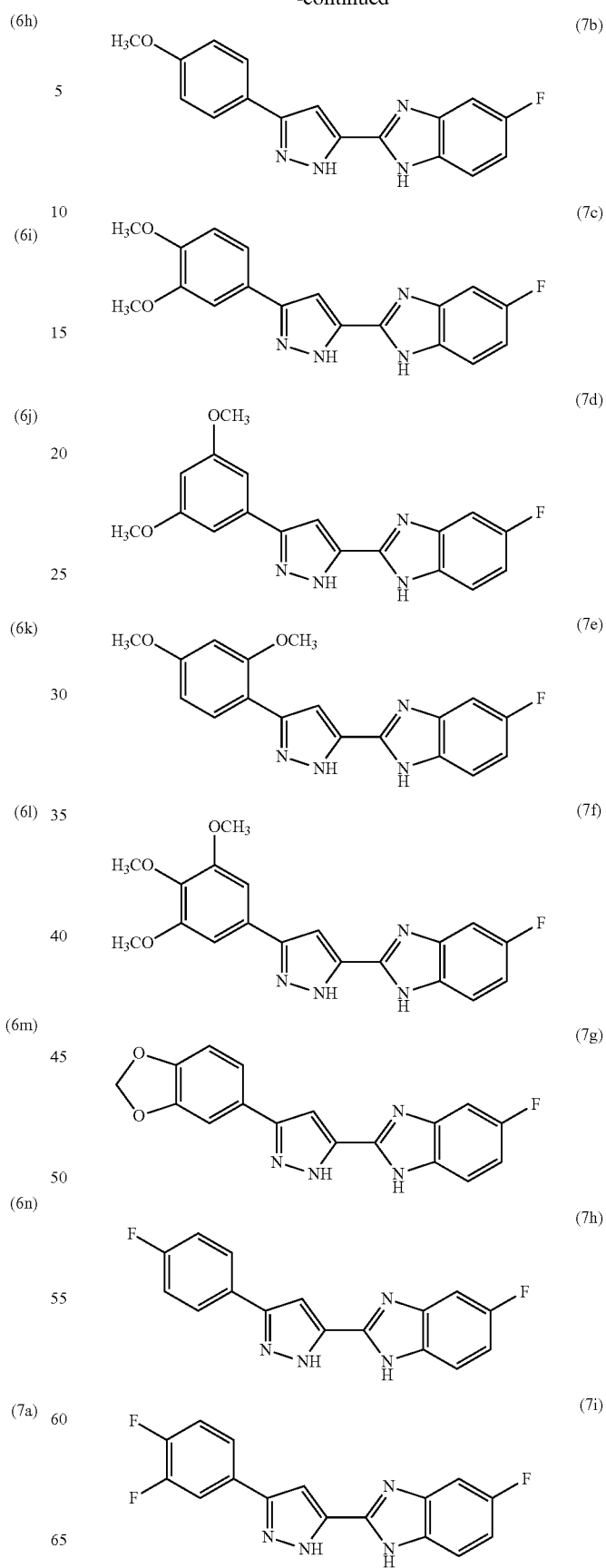

-continued (8m)
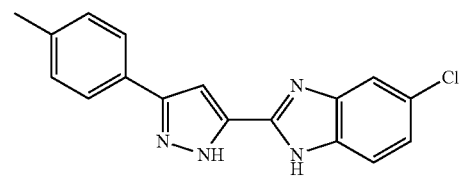
(8n)
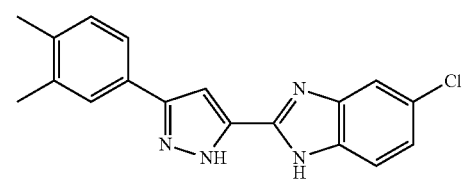
(9a)
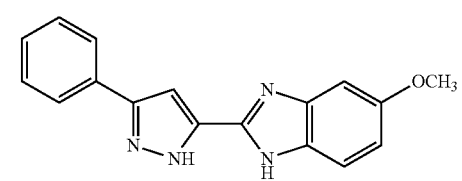
(9b)
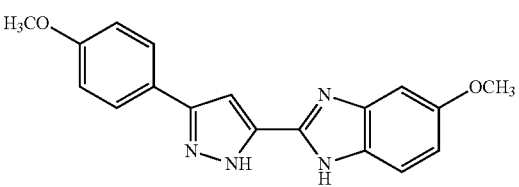
(9c)
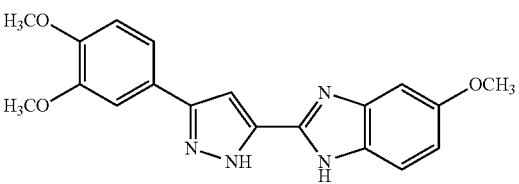
(9d)
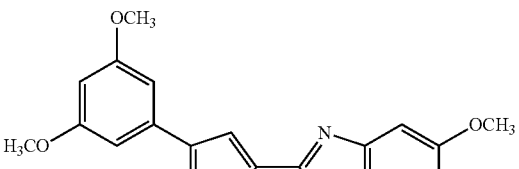
(9e)
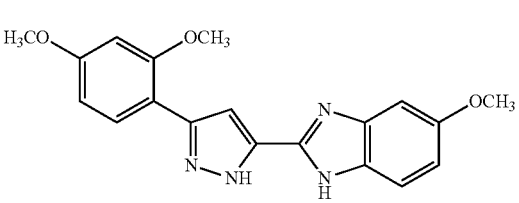
(9f)
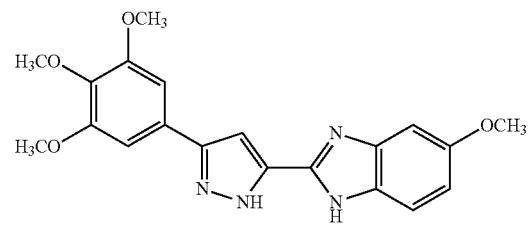
(9g)
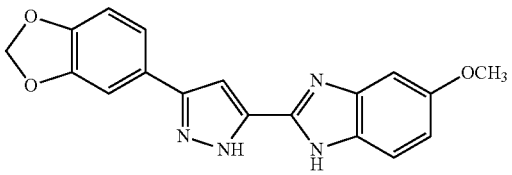
(9h)
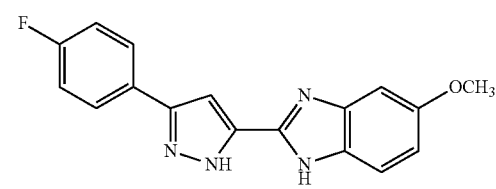
(9i)
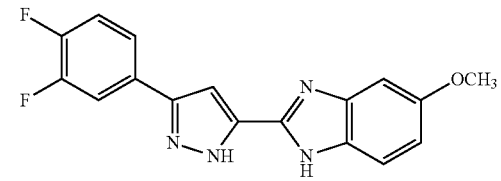
(9j)
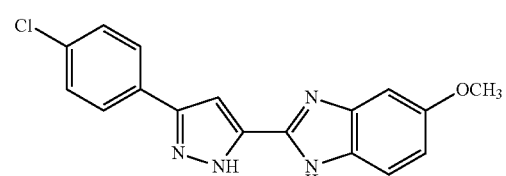
(9k)
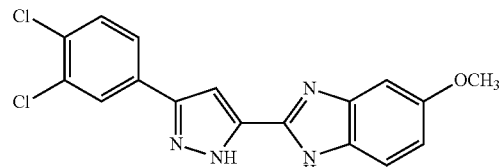
(9l)
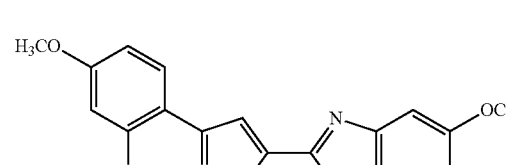
(9m)
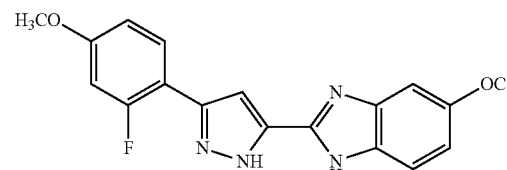

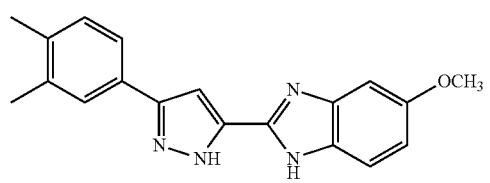 (9n)
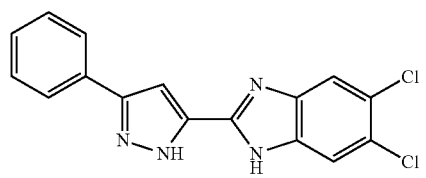 (10a)
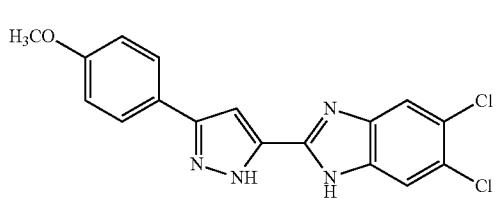 (10b)
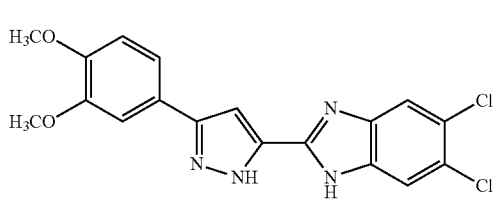 (10c)
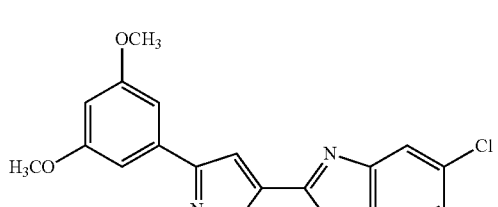 (10d)
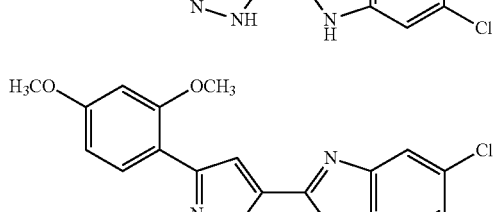 (10e)
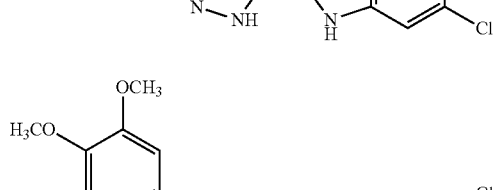 (10f)
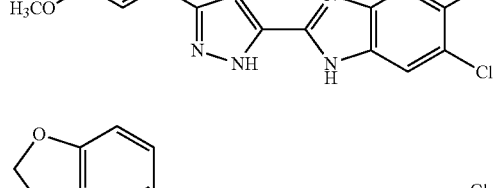 (10g)
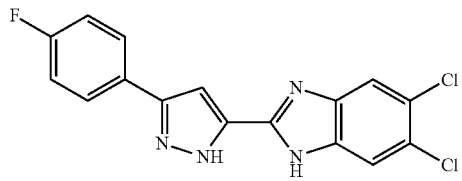 (10h)
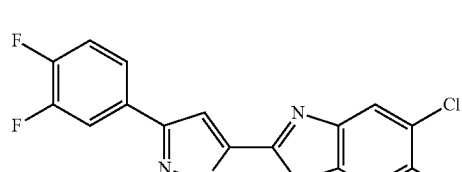 (10i)
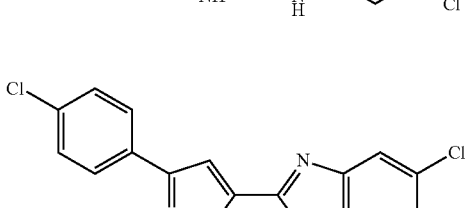 (10j)
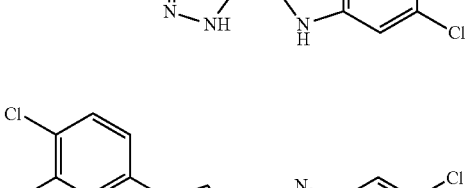 (10k)
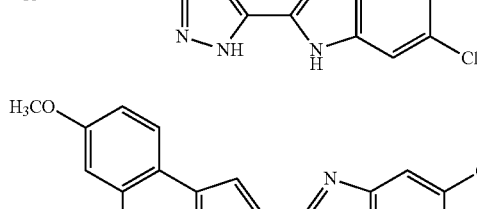 (10l)
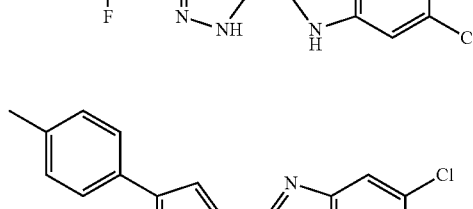 (10m)
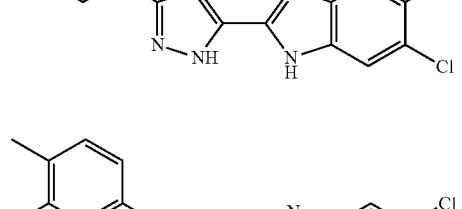 (10n)
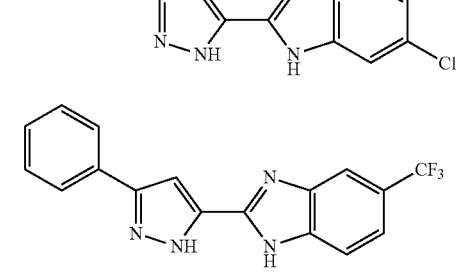 (11a)

-continued
(11b)
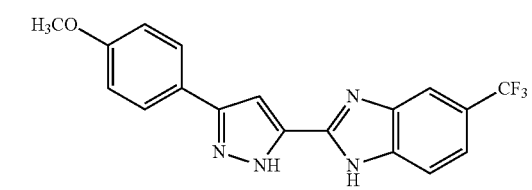
(11c)
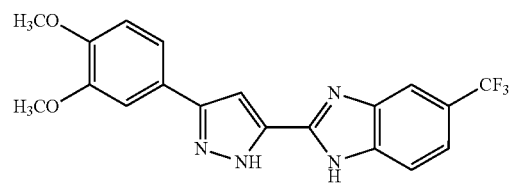
(11d)
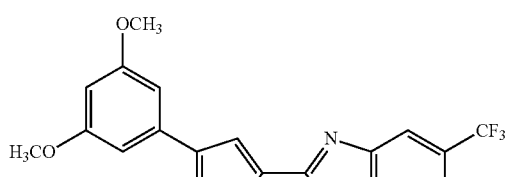
(11e)
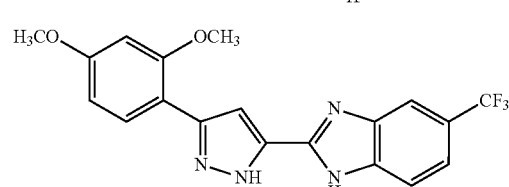
(11f)
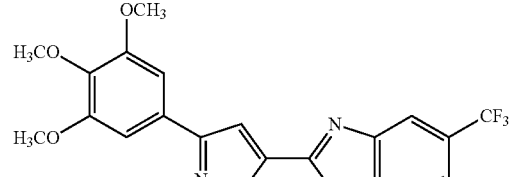
(11g)
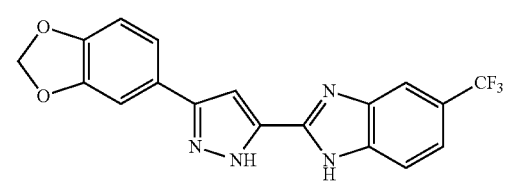
(11h)
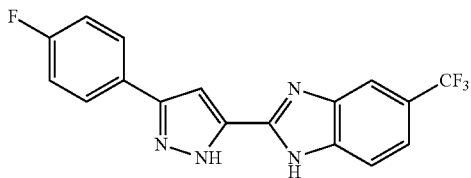
(11i)
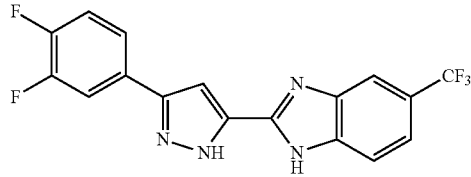
-continued
(11j)
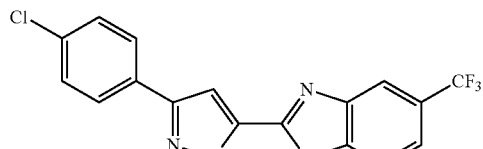
(11k)
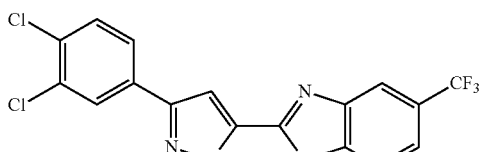
(11l)
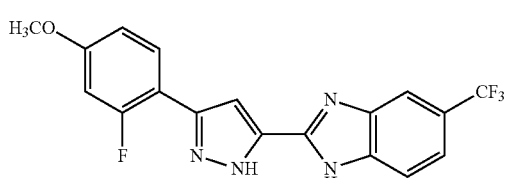
(11m)
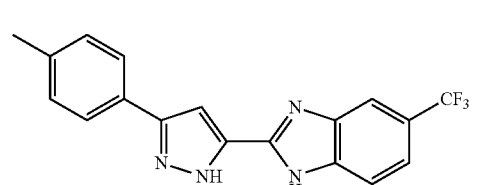
(11n)
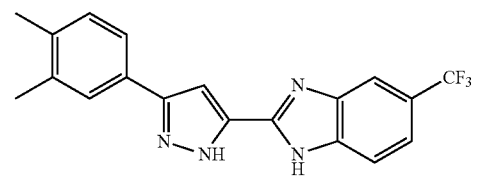
(12a)
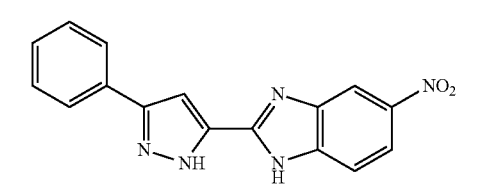
(12b)
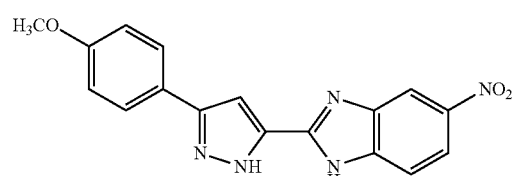
(12c)
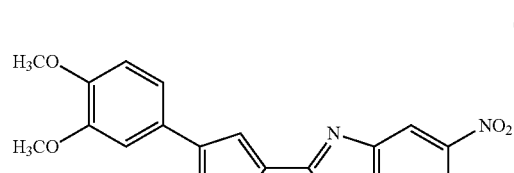

(12d) 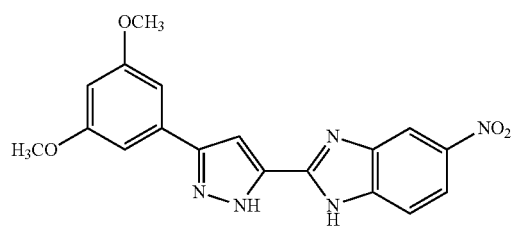
(12e) 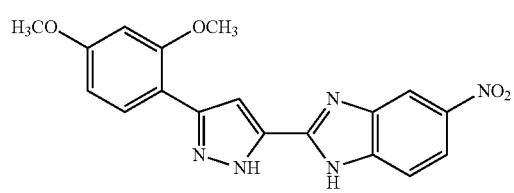
(12f) 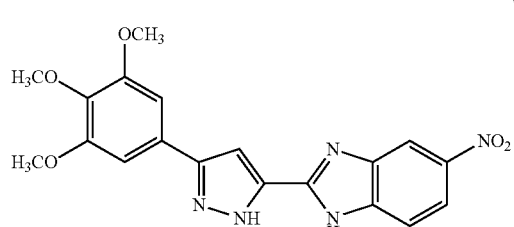
(12g) 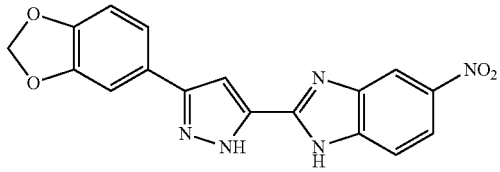
(12h) 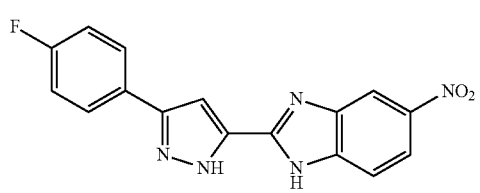
(12i) 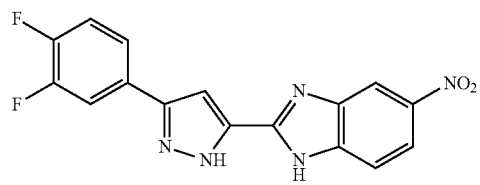
(12j) 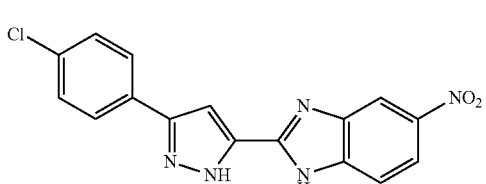
(12k) 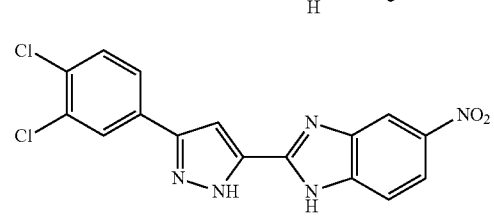
(12l) 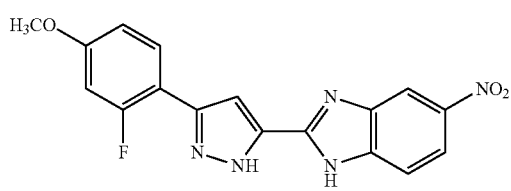
(12m) 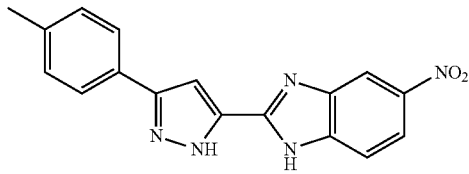
(12n) 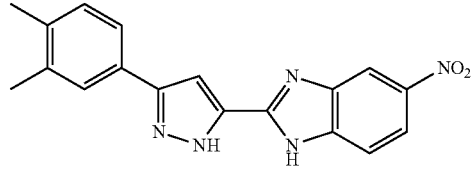
(13a) 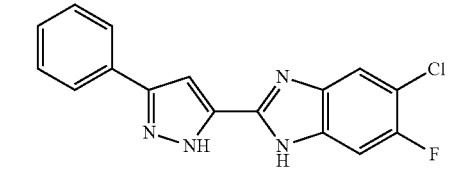
(13b) 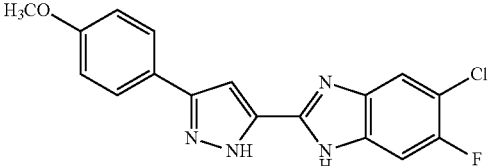
(13c) 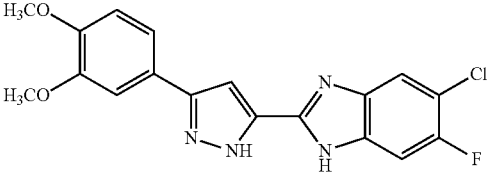
(13d) 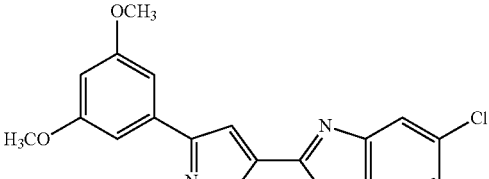
(13e) 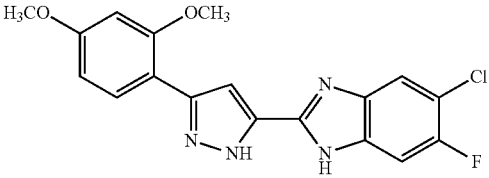

-continued
(13f) 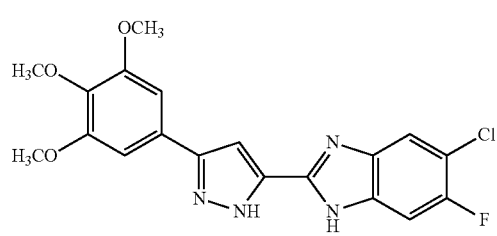
(13g) 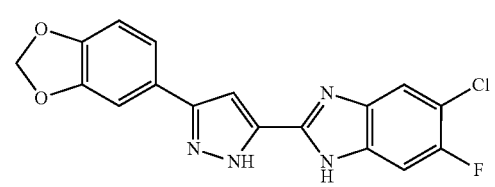
(13h) 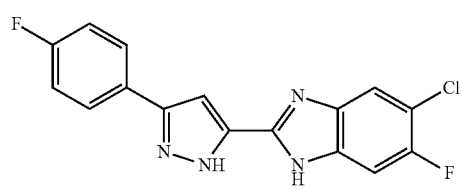
(13i) 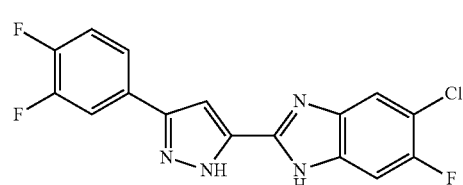
(13j) 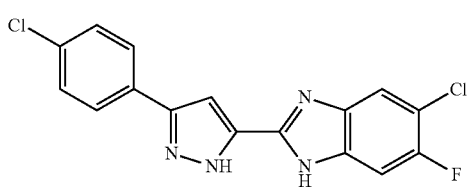
(13k) 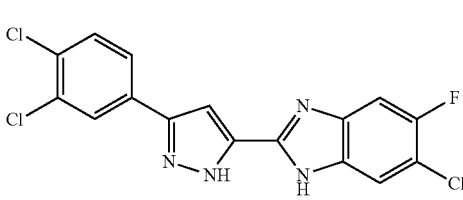
(13l) 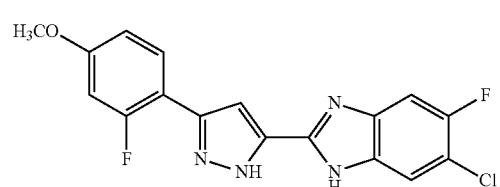
(13m) 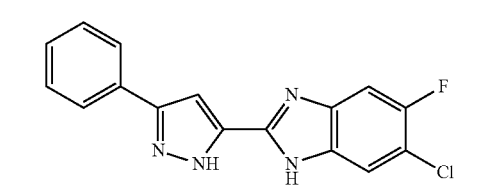
-continued
(13n) 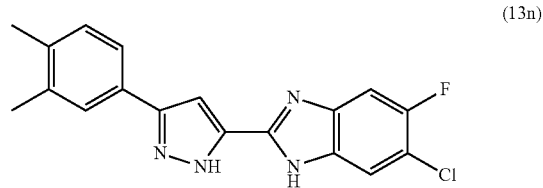
(14a) 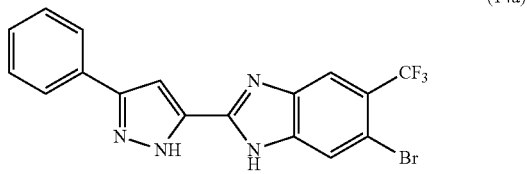
(14b) 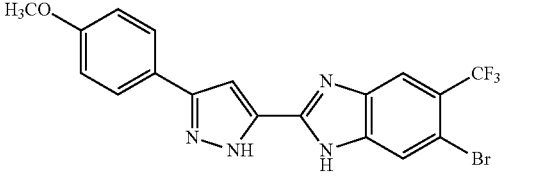
(14c) 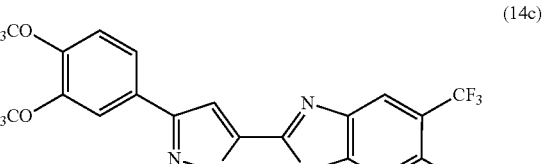
(14d) 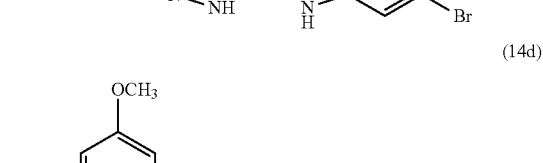
(14e) 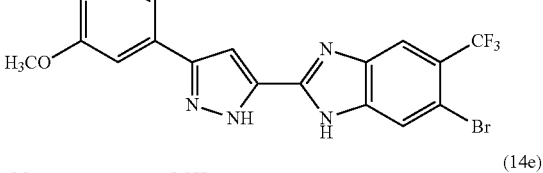
(14f) 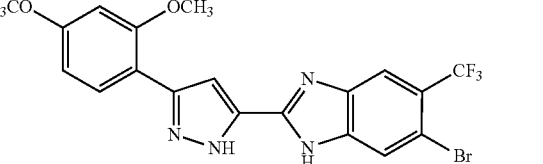
(14g) 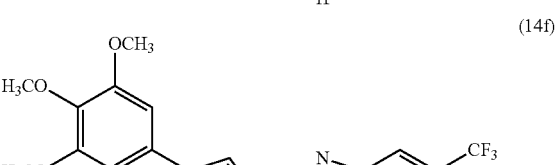
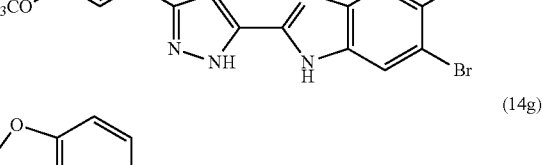
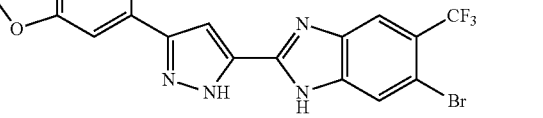

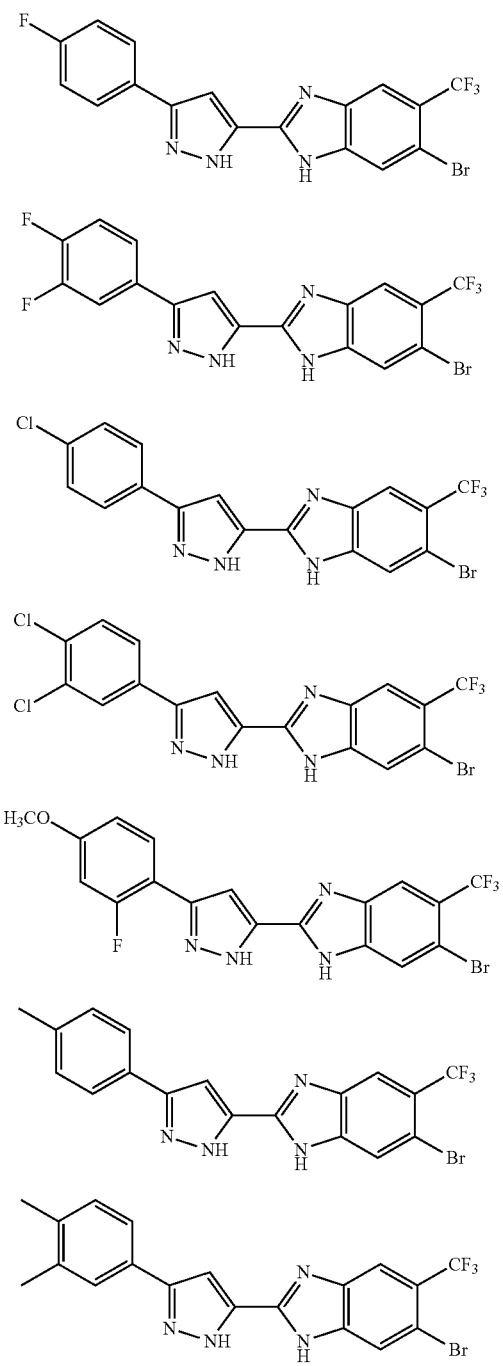

(14h)
(14i)
(14j)
(14k)
(14l)
(14m)
(14n)

The foregoing compounds so synthesized are useful as anticancer (anti-tumor) agents.

In the foregoing Scheme 1, the crucial intermediates for the preparation of precursors 3-phenyl-1H-pyrazole-5-carbaldehydes of formulae 5(a-n) are ethyl 3-phenyl-1H-pyrazole-5-carboxylates 4(a-n), which can be prepared using literature methods (A. Kamal, J. R. Tamboli, M. V. Vishnuvardhan, S. F. Adil, V. L. Nayak, S. Ramakrishna. Synthesis and anticancer activity of heteroaromatic linked 4β-amido podophyllotoxins as apoptotic inducing agents *Bioorg. Med. Chem. Lett.* 2013, 23, 273-280. S. Sidique, R. Ardecky, Y. Su, S. Narisawa, B. Brown, J. L. Milián, E. Sergienko, N. D. Cosford. Design and synthesis of pyrazole derivatives as potent and selective inhibitors of tissue-nonspecific alkaline phosphatase (TNAP). *Bioorg. Med. Chem. Lett.* 2009, 19 222-225).

The pyrazole-benzimidazole conjugates of the present invention have shown promising anticancer activity in various cell lines. The molecules synthesized are of immense biological significance. This resulted in design and synthesis of new congeners as illustrated in scheme 1 which comprises: oxidative cyclization of o-phenylenediamines of formulae 1, 2, 3, 4, 5, 6, 7, 8, 9, 10 and 3-phenyl-1H-pyrazole-5-carbaldehydes of formulae 5(a-n) and the compounds of formulae a, b, c, d, f, g, h, I, j, k, l, m, n, o, p for the compounds (6a-14a to 6n-14n).

1. Stirring the reaction mixtures at a temperature of 85° C. for 3-4 h to obtain the compounds (6a-14a to 6n-14n);
2. Synthesis of pyrazole linked benzimidazole conjugates; and
3. Purification by column chromatography using different solvents like ethyl acetate, hexane

EXAMPLES

The following examples are given by way of illustration and therefore should not be construed to the limit of the scope of the present invention.

Example 1

2-(3-(4-methoxyphenyl)-1H-pyrazol-5-yl)-1H-benzo[d]imidazole (6b)

3-(4-methoxyphenyl)-1H-pyrazole-5-carbaldehyde (5b) (202 mg, 1.0 mmol) in ethanol (10 mL) was added o-phenylenediamine (1) (108 mg, 1.0 mmol) and catalytic amount of Na2S2O5 (5 mg). The reaction mixture was stirred at a temperature of 85° C. for 3 h and the completion of reaction was confirmed by TLC. This reaction mixture was cooled to room temperature (28° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 2-(3-(4-methoxyphenyl)-1H-pyrazol-5-yl)-1H-benzo[d]imidazole (6b) (266 mg, 78% yield).

1H NMR (CDCl3+DMSO): 3.88 (s, 3H, OCH3), 6.99 (d, 2H, ArH, J=8.3 Hz), 7.17-7.29 (m, 3H, ArH) 7.53 (s, 1H, ArH), 7.63 (s, 1H, ArH), 7.72 (d, 2H, ArH, J=8.1 Hz) ppm. FABMS: 291 [M+H]+.

Example 2

2-(3-(3,4-dimethoxyphenyl)-1H-pyrazol-5-yl)-1H-benzo[d]imidazole (6c)

3-(3,4-dimethoxyphenyl)-1H-pyrazole-5-carbaldehyde (5c) (232 mg, 1.0 mmol) in ethanol (10 mL) was added o-phenylenediamine (1) (150 mg, 1.0 mmol) and catalytic amount of Na2S2O5 (5 mg). The reaction mixture was stirred at a temperature of 85° C. for 3 h and the completion of reaction was confirmed by TLC. This reaction mixture was cooled to room temperature (30° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 2-(3-(3,4-dimethoxyphenyl)-1H-pyrazol-5-yl)-1H-benzo[d]imidazole (6c) (255 mg, 79.5% yield).

1H NMR (CDCl3+DMSO): 3.91 (s, 3H, OCH3), 3.94 (s, 3H, OCH3) 6.97 (d, 1H, ArH, J=8.7 Hz), 7.18-7.24 (m, 3H, ArH) 7.4 (s, 1H, ArH), 7.58-7.68 (m, 2H, ArH)ppm. FABMS: 321 [M+H]+.

Example 3

2-(3-(3,4,5-trimethoxyphenyl)-1H-pyrazol-5-yl)-1H-benzo[d]imidazole (6f)

3-(3,4,5-trimethoxyphenyl)-1H-pyrazole-5-carbaldehyde (5f) (262 mg, 1.0 mmol) in ethanol (10 mL) was added o-phenylenediamine (1) (150 mg, 1.0 mmol) and catalytic amount of Na2S2O5 (5 mg). The reaction mixture was stirred at a temperature of 85° C. for 4 h and the completion of reaction was confirmed by TLC. This reaction mixture was cooled to room temperature (30° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 2-(3-(3,4,5-trimethoxyphenyl)-1H-pyrazol-5-yl)-1H-benzo[d]imidazole (60 (259 mg, 54% yield).

1H NMR (CDCl3+DMSO): 3.76 (s, 6H, OCH3), 3.84 (s, 3H, OCH3) 6.84 (s, 2H, ArH), 7.13-7.28 (m, 3H, ArH) 7.59 (s, 2H, ArH)ppm. FABMS: 351[M+H]+.

Example 4

2-(3-(benzo[d][1,3]dioxol-5-yl)-1H-pyrazol-5-yl)-1H-benzo[d]imidazole (6g)

3-(benzo[d][1,3]dioxol-5-yl)-1H-pyrazole-5-carbaldehyde (5g) (216 mg, 1.0 mmol) in ethanol (10 mL) was added o-phenylenediamine (1) (150 mg, 1.0 mmol) and catalytic amount of Na2S2O5 (5 mg). The reaction mixture was stirred at a temperature of 85° C. for 3 h and the completion of reaction was confirmed by TLC. This reaction mixture was cooled to room temperature (30° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 2-(3-(benzo[d][1,3]dioxol-5-yl)-1H-pyrazol-5-yl)-1H-benzo[d]imidazole (6g) (210 mg, 53.3% yield).

1H NMR (CDCl3+DMSO): 6.03 (s, 2H, OCH2O), 6.90 (d, 1H, ArH, J=7.9 Hz), 7.16 (s, 1H, ArH), 7.18-7.24 (m, 3H, ArH) 7.30 (s, 1H, ArH), 7.57-7.67 (m, 4H, ArH)ppm. FABMS: 305[M+H]+.

Example 5

5-fluoro-2-(3-(4-methoxyphenyl)-1H-pyrazol-5-yl)-1H-benzo[d]imidazole (7b)

3-(4-methoxyphenyl)-1H-pyrazole-5-carbaldehyde (5b) (202 mg, 1.0 mmol) in ethanol (10 mL) was added 4-fluorobenzene-1,2-diamine (2) (126 mg, 1.0 mmol) and catalytic amount of Na2S2O5 (5 mg). The reaction mixture was stirred at a temperature of 85° C. for 3 h and the completion of reaction was confirmed by TLC. This reaction mixture was cooled to room temperature (33° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 5-fluoro-2-(3-(4-methoxyphenyl)-1H-pyrazol-5-yl)-1H-benzo[d]imidazole (7b) (236 mg, 76.7% yield).

1H NMR (CDCl3+DMSO): 3.86 (s, 3H, OCH3) 6.98 (d, 1H, ArH, J=8.8 Hz), 7.16 (s, 1H, ArH), 7.47-7.58 (m, 3H, ArH) 7.71 (d, 2H, ArH, J=7.7 Hz)ppm. FABMS: 309[M+H]+.

Example 6

2-(3-(benzo[d][1,3]dioxol-5-yl)-1H-pyrazol-5-yl)-5-fluoro-1H-benzo[d]imidazole (7g)

3-(3,4,5-trimethoxyphenyl)-1H-pyrazole-5-carbaldehyde (5f) (262 mg, 1.0 mmol) in ethanol (10 mL) was added 4-fluorobenzene-1,2-diamine (2) (126 mg, 1.0 mmol) and catalytic amount of Na2S2O5 (5 mg). The reaction mixture was stirred at a temperature of 85° C. for 4 h and the completion of reaction was confirmed by TLC. This reaction mixture was cooled to room temperature (28° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 2-(3-(benzo[d][1,3]dioxol-5-yl)-1H-pyrazol-5-yl)-5-fluoro-1H-benzo[d]imidazole (7g) (257 mg, 80% yield).

1H NMR (CDCl3+DMSO): 6.03 (s, 2H, OCH2O), 6.89 (d, 1H, ArH, J=8.1 Hz), 7.12 (s, 1H, ArH), 7.23-7.33 (m, 2H, ArH) 7.61 (d, 2H, ArH, J=8.1 Hz)ppm. FABMS: 305[M+H]+.

Example 7

5-chloro-2-(3-(3,4,5-trimethoxyphenyl)-1H-pyrazol-5-yl)-1H-benzo[d]imidazole (8f)

3-(3,4,5-trimethoxyphenyl)-1H-pyrazole-5-carbaldehyde (5f) (262 mg, 1.0 mmol) in ethanol (10 mL) was added 4-chlorobenzene-1,2-diamine (3) (142.9 mg, 1.0 mmol) and catalytic amount of Na2S2O5 (5 mg). The reaction mixture was stirred at a temperature of 85° C. for 4 h and the completion of reaction was confirmed by TLC. This reaction mixture was cooled to room temperature (30° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 5-chloro-2-(3-(3,4,5-trimethoxyphenyl)-1H-pyrazol-5-yl)-1H-benzo[d]imidazole (80 (291 mg, 76% yield).

1H NMR (CDCl3+DMSO): 3.85 (s, 3H, OCH3), 3.94 (s, 6H, OCH3) 7.08 (s, 2H, ArH), 7.18 (d, 1H, ArH, J=8.6 Hz) 7.24 (s, 2H, ArH), 7.50-7.62 (m, 1H, ArH) 7.64 (s, 1H, ArH)ppm. FABMS: 385[M+H]+

Example 8

5-methoxy-2-(3-(3,4,5-trimethoxyphenyl)-1H-pyrazol-5-yl)-1H-benzo[d]imidazole (9f)

3-(3,4,5-trimethoxyphenyl)-1H-pyrazole-5-carbaldehyde (5f) (262 mg, 1.0 mmol) in ethanol (10 mL) was added 4-methoxybenzene-1,2-diamine (4) (138 mg, 1.0 mmol) and catalytic amount of Na2S2O5 (5 mg). The reaction mixture was stirred at a temperature of 85° C. for 4 h and the completion of reaction was confirmed by TLC. This reaction mixture was cooled to room temperature (35° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 5-methoxy-2-(3-(,4,5-trimethoxyphenyl)-1H-pyrazol-5-yl)-1H-benzo[d]imidazole (90 (292 mg, 77 yield).

1H NMR (CDCl3+DMSO): 3.87 (s, 6H, OCH3), 3.93 (s, 6H, OCH3) 6.82-6.92 (m, 1H, ArH) 7.06 (s, 2H, ArH), 7.23 (s, 1H, ArH) 7.50 (s, 1H, ArH) ppm. FABMS: 381[M+H]+.

Example 9

5,6-dichloro-2-(3-(4-methoxyphenyl)-1H-pyrazol-5-yl)-1H-benzo[d]imidazole (10b)

3-(4-methoxyphenyl)-1H-pyrazole-5-carbaldehyde (5b) (202 mg, 1.0 mmol) in ethanol (10 mL) was added 4,5-dichlorobenzene-1,2-diamine (5) (177 mg, 1.0 mmol) and catalytic amount of Na2S2O5 (5 mg). The reaction mixture was stirred at a temperature of 85° C. for 3 h and the completion of reaction was confirmed by TLC. This reaction mixture was cooled to room temperature (30° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 5,6-dichloro-2-(3-(4-methoxyphenyl)-1H-pyrazol-5-yl)-1H-benzo[d]imidazole (10b) (270 mg, 75.4% yield).

1H NMR (CDCl3+DMSO): 3.86 (s, 3H, OCH3), 6.98 (d, 2H, ArH, J=8.4 Hz) 7.15 (s, 1H, ArH) 7.53 (s, 2H, ArH), 7.70 (d, 2H, ArH, J=7.4 Hz) ppm. FABMS: 418[M+H]+.

Example 10

5,6-dichloro-2-(3-(3,4,5-trimethoxyphenyl)-1H-pyrazol-5-yl)-1H-benzo[d]imidazole (10f)

3-(4-methoxyphenyl)-1H-pyrazole-5-carbaldehyde (5b) (202 mg, 1.0 mmol) in ethanol (10 mL) was added 4,5-dichlorobenzene-1,2-diamine (5) (177 mg, 1.0 mmol) and catalytic amount of Na2S2O5 (5 mg). The reaction mixture was stirred at a temperature of 85° C. for 4 h and the completion of reaction was confirmed by TLC. This reaction mixture was cooled to room temperature (33° C.) and extracted with ethyl acetate (3×30 mL). The combined organic layers were washed with water, brine solution and dried over anhydrous Na2SO4. Evaporation of the solvent under vacuum yielded the crude product that was further purified by column chromatography using ethyl acetate/hexane to afford the pure compound of 5,6-dichloro-2-(3-(3,4,5-trimethoxyphenyl)-1H-pyrazol-5-yl)-1H-benzo[d]imidazole (1 Of) (330 mg, 79% yield).

1H NMR (CDCl3+DMSO): 3.84 (s, 3H, OCH3), 3.93 (s, 6H, OCH3) 7.07 (s, 2H, ArH) 7.23 (s, 1H, ArH) 7.70 (s, 2H, ArH) ppm. FABMS: 418[M+H]+.

Cytotoxic activity: The human cancer cell line assays for some representative compounds were carried out at the National Cancer Institute, Maryland, USA.

The pyrazole linked benzimidazole conjugates (6f, 6g, 7g, 8f, 9f and 10f) have been tested against fifty six human tumor cell lines derived from nine cancer types (leukemia, non-small cell lung cancer, colon cancer, CNS cancer, melanoma, ovarian cancer, renal cancer, prostate cancer and breast cancer) as per the NCI protocol. For each compound, dose response curves for individual cell lines have been measured at a minimum of five concentrations at 10 fold dilutions. A protocol of 48 h continuous drug exposure has been used, and a sulforhodamine B (SRB) protein assay was used to estimate cell viability or growth. Nocodazole was used as standard and the Log 10 GI50 values have been reported in the table 1. The concentration for 50% cell growth inhibition (GI50) (Growth Inhibition) total cell growth inhibition (TGI, 0% growth) (Total Growth Inhibition), and 50% cell death (LC50, 50% growth) (Lethal concentration) values were tabulated (Table-1). DMSO used as control to calculate the values of GI50, LC50, TGI. The compounds 6f, 6g, 7g, 8f, 9f and 10f has been evaluated for their in vitro cytotoxicity in fifty six cell lines from nine human cancer types of leukemia (K-562, SR), lung (Hop-62, NCI-H226, NCI-H522), colon (HCT-116, HCT-15, HCC-2998), CNS (SF-539), melanoma (SK-MEL-5, UACC-62, M14), ovarian (IGROV1), renal (A498), prostate (PC3) breast (BT-549, MDA-MB-435, HS578T) origin. The results are expressed as percent of cell growth determined relative to that of untreated control cells (Table 2). The representative compounds 6f, 6g, 7g, 8f, 9f and 10f showed significant anticancer activity against some cancer cell lines.

TABLE 1

Log10 GI50 (concentration in mol/L causing 50% growth inhibition) values for pyrazole- benzimidazole conjugates (6f, 6g, 7g, 8f, 9f and 10f) each cancer type represents the average of six to eight different cancer cell lines.

| Cell Lines | Log10 GI50 | | | | | | |
|---|---|---|---|---|---|---|---|
| | 6f | 6g | 7g | 8f | 9f | 10f | Nocodazole |
| Leukemia | −5.64 | −5.60 | −5.53 | −5.61 | −5.90 | −5.56 | −7.91 |
| Non-small-cell lung | −5.62 | −5.34 | −5.27 | −5.56 | −5.83 | −5.53 | −7.69 |
| Colon | −5.32 | −5.39 | −5.27 | −5.40 | −5.64 | −5.44 | −7.75 |
| CNS | −5.28 | −5.37 | −5.20 | −5.43 | −5.61 | −5.45 | −7.64 |
| Melanoma | −5.68 | −5.52 | −5.34 | −5.61 | −5.88 | −5.55 | −7.65 |
| Ovarian | −5.49 | −5.36 | −5.21 | −5.45 | −5.69 | −5.35 | −6.84 |
| Renal | −5.58 | −5.69 | −5.34 | −5.50 | −5.65 | −5.45 | −6.97 |
| Prostate | −5.54 | −5.29 | −5.25 | −5.54 | −5.81 | −5.52 | −7.84 |
| Breast Cancer | −5.65 | −5.47 | −5.44 | −5.59 | −5.94 | −5.50 | −6.81 |

The compounds 6f, 6g, 7g, 8f, 9f and 10f exhibited a broad spectrum of anticancer activity against fifty six cell lines in nine cell panels, with GI50 value range of 0.34-10 μM. Particularly, the compounds 8f and 9f were more potent than the compounds 6f, 6g, 7g and 10f against all the cell lines tested. In detail, the GI50 values for the compound 6f against leukemia RPMI-8226 cell line were 1.20 μM. In the non-small cell lung cancer panel, the growth of NCI-H226 and NCI-H522 cell lines were affected by compound 6f with GI50 values as 1.14 and 1.84 μM, respectively. The GI50 values for the compound 6f against melanoma cancer cell line SK-MEL-5 was 1.34 μM. whereas the Ovarian cancer cell line OVCAR-4 and OVCAR-5 were affected by the compound 6f with GI50 value of 1.26 μM and 1.30 μM respectively. The breast cancer cells such as T-47D were also affected by the compound 6f with GI50 value 1.11 μM. The GI50 values for compound 6g against leukemia RPMI-8226 cell line was 1.14 μM. In the CNS cancer panel the cell line SNB-75 was affected by 6g with GI50 value 1.01 μM and the GI50 values for the compound 6g against renal cancer cell line TK-10 is 1.09 μM. In the melanoma cancer panel, the growth of SK-MEL-5 and UACC-254 cell lines were affected by compound 7g with GI50 values as 1.46 and 1.02 μM, respectively. The GI50 values for the compound 7g against leukemia RPMI-8226 1.09 μM. whereas in the ovarian cancer panel the cell line OVCAR-4 growth was affected by 7g with GI50 value 1.37 μM. The GI50 values for the compound 8f against leukemia RPMI-8226 cell line was 1.65 μM. In the ovarian cancer panel, the growth of cell lines OVCAR-4 and OVCAR-5 were affected by compound 8f with GI50 values 1.38 and 1.21 μM, respectively. The GI50 values for the compound 9f against leukemia RPMI-8226, MOLT-4 and CCRF-CEM were 0.64, 0.73 and 1.29 μM respectively. In the non-small cell lung cancer panel, the growth of NCI-H226, NCI-H23 and NCI-H522 cell lines were affected by compound 9f with GI50 values as 0.46, 1.34 and 1.21 μM respectively. The GI50 values for the compounds 9f against melanoma cancer, the growth of SK-MEL-5 and UACC-62 cell lines were 4.62 and 1.12 μM, respectively. The GI50 values for the compound 9f against ovarian OVCAR-4 and OVCAR-8 were 1.24 and 1.15 μM, respectively. The Prostate cancer cell line PC-3 was affected by the compound 9f with GI 50 value 1.03 μM. The breast cancer cell lines BT-549, T-47D and MDA-MB-468 were affected by the compound 9f with GI 50 values 0.89, 0.34 and 0.38 μM, respectively. The GI50 values for the compound 10f against leukemia RPMI-8226 cell line was 1.75 μM. Overall the compound 9f exhibited potential growth inhibitory activity against breast cancer and leukemia cell lies.

Compounds 6f, 6g, 7g, 8f, 9f and 10f exhibited activity against fifty six cell lines in nine cancer cell panels with GI50 values of <10 μm. In vitro cytotoxicity of compounds 6f, 6g, 7g, 8f, 9f and 10f in the selected cancer cell lines has been illustrated in Table 2.

TABLE 2

Cytotoxicity of compounds 6f, 6g, 7g, 8f, 9f and 10f in a panel of fifty six cancer cell lines.

| Cancer panel/ cell line | GI50 values (μM) | | | | | |
|---|---|---|---|---|---|---|
| | 6f | 6g | 7g | 8f | 9f | 10f |
| Leukemia | | | | | | |
| CCRF-CEM | 2.12 | 2.52 | 2.65 | 2.48 | 1.29 | 2.35 |
| HL-60(TB) | 2.54 | 2.27 | 2.74 | 2.49 | 1.69 | 3.34 |
| K-562 | 3.08 | 3.83 | 4.81 | 3.04 | 2.01 | 3.30 |
| MOLT-4 | 2.13 | 2.68 | 3.14 | 2.02 | 0.73 | 2.49 |
| RPMI-8226 | 1.20 | 1.14 | 1.09 | 1.65 | 0.64 | 1.75 |
| SR | 3.32 | 3.37 | 4.95 | 3.32 | 1.74 | 3.89 |
| Non-small cell lung | | | | | | |
| A549/ATCC | 2.43 | 4.23 | 3.53 | 2.96 | 1.63 | 2.87 |
| HOP-62 | 3.54 | 8.46 | 8.54 | 3.11 | 2.02 | 3.43 |
| HOP92 | NT | NT | NT | NT | NT | NT |
| NCI-H226 | 1.14 | 4.42 | 4.21 | 1.88 | 0.46 | 2.29 |
| NCI-H23 | 2.26 | 4.47 | 8.84 | 2.73 | 1.34 | 3.40 |
| NCIH322M | 2.85 | 6.29 | 6.88 | 3.65 | 2.47 | 3.29 |
| NCI-H460 | 3.64 | 4.57 | 6.06 | 3.65 | 2.64 | 3.33 |
| NCI-H522 | 1.87 | 1.98 | 2.56 | 1.90 | 1.21 | 2.02 |
| Colon | | | | | | |
| COLO-205 | 3.98 | 4.78 | 8.11 | 3.18 | 1.61 | 3.77 |
| HCC-2998 | 7.10 | 3.74 | 5.37 | 5.98 | 3.03 | 4.47 |
| HCT-116 | 3.15 | 6.36 | 4.50 | 3.45 | 1.81 | 2.78 |
| HCT-15 | 3.43 | 3.86 | 3.73 | 2.90 | 2.50 | 2.89 |
| HT29 | 7.16 | 3.66 | 5.77 | 4.14 | 2.76 | 3.42 |
| KM12 | 3.15 | 1.75 | 2.96 | 3.45 | 1.70 | 3.56 |
| SW-620 | 7.73 | 5.87 | 9.34 | 4.99 | 2.89 | 4.47 |
| CNS | | | | | | |
| SF-268 | 6.43 | 4.77 | 6.05 | 3.60 | 2.74 | 3.95 |
| SF-295 | 3.13 | 3.24 | 4.20 | 2.35 | 1.62 | 3.04 |
| SF-539 | 5.11 | 2.71 | 2.90 | 4.66 | 2.42 | 3.28 |
| SNB-19 | 1.78 | 5.92 | 10.0 | 7.25 | 2.98 | 5.47 |
| SNB-75 | 2.83 | 1.01 | 2.80 | 2.71 | 2.23 | 3.12 |
| U251 | 3.73 | 2.37 | 2.78 | 3.38 | 2.90 | 2.97 |
| Melanoma | | | | | | |
| LOX IMVI | NT | NT | NT | NT | NT | NT |
| MALME-3M | 1.95 | 2.33 | 2.75 | 2.58 | 1.74 | 2.70 |
| M14 | 2.57 | 2.19 | 4.17 | 2.92 | 1.66 | 3.57 |
| MDA-MB-435 | 2.35 | 3.12 | 5.43 | 3.30 | 1.49 | 3.78 |
| SK-MEL-2 | NT | NT | NT | NT | NT | NT |
| SK-MEL-28 | 2.72 | 4.85 | 8.87 | 2.42 | 1.90 | 3.07 |
| SK-MEL-5 | 1.34 | 1.53 | 1.46 | 1.62 | 0.46 | 1.56 |
| UACC-257 | 2.10 | 6.00 | 1.02 | 2.60 | 1.67 | 3.77 |
| UACC-62 | 1.64 | 3.08 | 4.77 | 1.97 | 1.12 | 1.94 |
| Ovarian | | | | | | |
| IGROV1 | 2.34 | 3.66 | 3.67 | 3.42 | 1.90 | 3.86 |
| OVCAR-3 | 4.00 | 3.21 | 5.32 | 3.50 | 2.05 | 4.05 |
| OVCAR-4 | 1.26 | 2.16 | 1.37 | 1.38 | 1.24 | 2.21 |
| OVCAR-5 | 1.30 | 1.49 | 6.44 | 1.21 | 3.03 | 7.08 |
| OVCAR-8 | 2.35 | 3.97 | 3.43 | 2.26 | 1.15 | 2.51 |
| NCI/ADR-RES | 2.88 | 4.08 | 4.43 | 3.16 | 2.91 | 3.25 |
| SK-OV-3 | 3.48 | 4.98 | 1.24 | 4.47 | 2.83 | 1.73 |
| Renal | | | | | | |
| 786-0 | 3.66 | 4.58 | 7.13 | 5.32 | 2.92 | 4.09 |
| A498 | 1.51 | 1.70 | 4.66 | 2.10 | 2.23 | 4.21 |
| ACHN | 2.77 | 4.33 | 3.64 | 2.96 | 2.63 | 3.54 |
| CAKI-1 | 2.24 | 2.74 | 2.71 | 2.80 | 1.79 | 3.81 |
| RXF 393 | 1.77 | 2.36 | 3.02 | 3.26 | 2.49 | 3.17 |
| SN12C | 3.91 | 3.73 | 4.95 | 3.06 | 2.06 | 3.05 |
| TK-10 | 4.07 | 1.09 | 1.30 | 3.52 | 2.21 | 4.61 |
| UO-31 | 2.21 | 3.98 | 2.93 | 2.64 | 1.57 | 2.47 |
| Prostate | | | | | | |
| PC-3 | 2.10 | 3.64 | 3.78 | 2.47 | 1.03 | 2.20 |
| DU-145 | 3.90 | 7.27 | 8.24 | 3.27 | 2.29 | 4.16 |
| Breast | | | | | | |
| MCF7 | 2.79 | 3.78 | 3.53 | 2.17 | 2.15 | 2.79 |
| MDA-MB-231/ATCC | 3.22 | 4.12 | 2.22 | 3.94 | 2.87 | 4.14 |
| HS 578T | 6.89 | 3.80 | 9.53 | 3.58 | 2.89 | 4.53 |
| BT-549 | 1.80 | 2.12 | 2.16 | 2.54 | 0.89 | 2.84 |
| T-47D | 1.11 | 3.32 | 3.21 | 1.58 | 0.34 | 1.87 |
| MDA-MB-435 | 0.93 | 3.57 | 4.14 | 2.33 | 0.38 | 3.49 |

*NT = not tested

The mean graph midpoint values of Log 10 TGI and Log 10 LC50 as well as Log 10 GI50 for compounds 6f, 6g, 7g, 8f, 9f and 10f is listed in Table-3. As demonstrated by mean graph pattern, compounds 7e, 8e, 10e, 11e, 12e, 13e and 8f exhibited an interesting profile of activity and selectivity for various cell lines. The mean graph mid points of Log 10 TGI and Log 10 LC50 have shown similar pattern to the log 10 GI50 mean graph mid points.

TABLE 3

Log10 GI50, Log10 TGI and Log10 LC50 mean graphs midpoints(MG_MID) of in vitro cytotoxicity data for the compound 6f, 6g, 7g, 8f, 9f and 10f against human tumor cell lines.

| Compound | Log10 GI50 | Log10 TGI | Log10 LC50 |
|---|---|---|---|
| 6f | −5.54 | −4.83 | −4.2 |
| 6g | −5.43 | −4.75 | −4.25 |
| 7g | −5.32 | −4.19 | −4.03 |
| 8f | −5.52 | −4.93 | −4.34 |
| 9f | −5.77 | −5.17 | −4.53 |
| 10f | −5.48 | −4.88 | −4.26 |

Since pyrazole and benzimidazole moieties individually contribute remarkable functions in the field of medicinal chemistry, the efforts of the present invention projected towards the synthesis of pyrazole linked benzimidazole conjugates as single molecular scaffold. All the conjugates achieved pure and good yields by column chromatography using ethyl acetate and hexane solvent system. The conjugates of the present invention displayed remarkable anticancer potentials against a panel of 60 cancer cell lines. Some of the conjugates, such as 6f, 6g, 7g, 8f, 9f and 10f, demonstrated pronounced activities in most of the cells investigated especially in breast cancer cells.

The present invention provides some new pyrazole linked benzimidazole conjugates useful as antitumor agents. The present invention also provides a process for the preparation of novel pyrazole linked benzimidazole conjugates.

The invention claimed is:

1. A composition comprising:
a pyrazole linked benzimidazole conjugate of Formula A and salts thereof

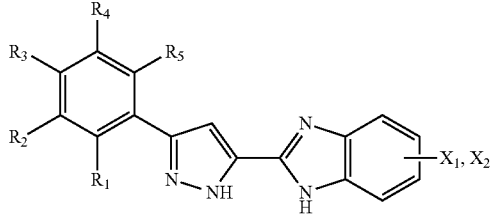

Formula A wherein $R_1$ is H;
wherein $R_2$ is chosen from H, $OCH_3$ and 3,4($OCH_2O$);
wherein $R_3$ is chosen from $OCH_3$ and 3,4($OCH_2O$);
wherein $R_4$ is chosen from H, and $OCH_3$;
wherein $R_5$ is H;
wherein $X_1$ is chosen from H, Cl, F, and $OCH_3$;
wherein $X_2$ is chosen from H, Cl; and
wherein when $R_3$ is $OCH_3$, only one of $X_1$ or $X_2$ can be H.

2. The composition of claim 1, wherein the pyrazole linked benzimidazole conjugate of Formula A is chosen from:

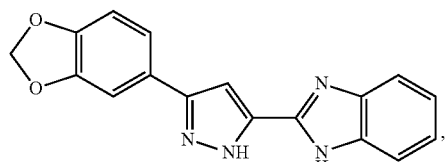
(6g)

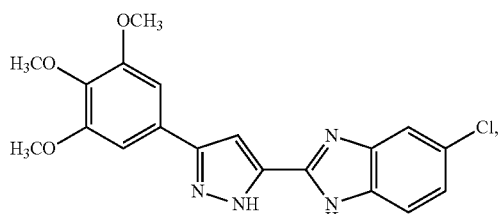
(8f)

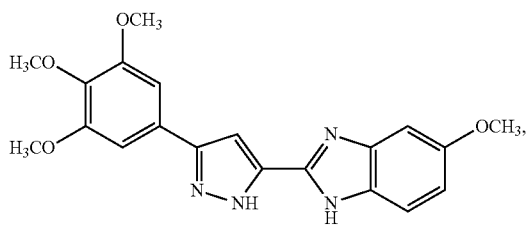
(9f)

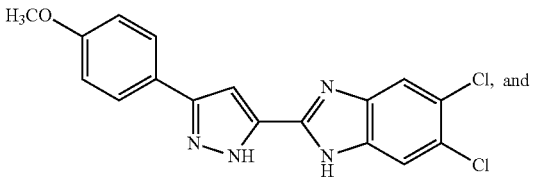
(10b)

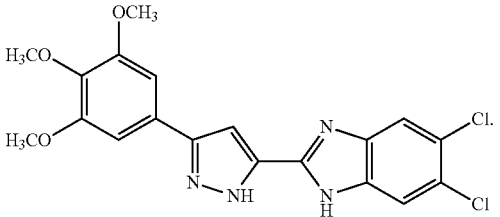
(10f)

3. The composition of claim 1, wherein the composition is provided in a dosage to have anticancerous activity.

4. The composition of claim 3, wherein the composition is provided in a dosage to have anticancerous activity against a cell line selected from the group consisting of leukemia, non-small cell lung cancer, colon cancer, CNS cancer, melanoma, ovarian cancer, renal cancer, prostate cancer and breast cancer.

5. The composition of claim 2, wherein the composition is provided in a dosage to have anticancerous activity.

6. The composition of claim 5, wherein the composition is provided in a dosage to have anticancerous activity against a cell line selected from the group consisting of leukemia, non-small cell lung cancer, colon cancer, CNS cancer, melanoma, ovarian cancer, renal cancer, prostate cancer and breast cancer.

* * * * *